US008123671B2

(12) United States Patent
Evans

(10) Patent No.: US 8,123,671 B2
(45) Date of Patent: Feb. 28, 2012

(54) PELVIC IMPLANT SYSTEMS AND METHODS

(75) Inventor: Doug Evans, Snellville, GA (US)

(73) Assignee: C.R. Bard, Inc., Murray Hill, NJ (US)

( * ) Notice: Subject to any disclaimer, the term of this patent is extended or adjusted under 35 U.S.C. 154(b) by 693 days.

(21) Appl. No.: 11/993,375

(22) PCT Filed: Aug. 3, 2006

(86) PCT No.: PCT/US2006/030370
§ 371 (c)(1),
(2), (4) Date: Feb. 6, 2009

(87) PCT Pub. No.: WO2007/016698
PCT Pub. Date: Feb. 8, 2007

(65) Prior Publication Data
US 2010/0234679 A1 Sep. 16, 2010

Related U.S. Application Data

(60) Provisional application No. 60/810,065, filed on Jun. 1, 2006, provisional application No. 60/705,569, filed on Aug. 4, 2005, provisional application No. 60/705,624, filed on Aug. 4, 2005.

(51) Int. Cl.
A61F 2/00 (2006.01)
(52) U.S. Cl. ........................................... 600/30; 600/37
(58) Field of Classification Search .............. 600/29–32, 600/37; 128/DIG. 25; 606/119, 148, 151–158, 606/222–225
See application file for complete search history.

(56) References Cited

U.S. PATENT DOCUMENTS

| 107,956 A | 10/1870 | Peoble |
| 1,393,107 A | 10/1921 | Fuller |
| 1,924,348 A | 8/1933 | Brown |
| 2,042,403 A | 5/1936 | Hrivnak |
| 2,641,249 A | 6/1953 | Brockman |
| 2,666,338 A | 1/1954 | Sandberg |
| 3,453,729 A | 7/1969 | Larson |
| 3,714,843 A | 2/1973 | Bracey |

(Continued)

FOREIGN PATENT DOCUMENTS

DE 3223153 C1 8/1983

(Continued)

OTHER PUBLICATIONS

Jul. 20, 2007 International Search Report from application PCT/US2006/030370.

(Continued)

Primary Examiner — John Lacyk
(74) Attorney, Agent, or Firm — Rutan & Tucker, LLP

(57) ABSTRACT

Systems and methods for implanting pelvic implants (10) In one embodiment, an anterior implant (10) has multiple arms (14, 16, 18, 20) that extend outwardly from a body portion (12) of the implant (10) in opposite directions In one embodiment, a posterior implant (10) has multiple arms (14, 16, 18, 20) that generally extend in the same direction In one embodiment, an anterior introducer (170) includes a needle (178) having a curved section (182) that is sized and configured for implanting an anterior prolapse implant (78) In one embodiment, a posterior introducer (170) includes a needle (178) having a curved section (182) that has a first curved portion (184 and a second curved portion, (186) the two curved portions having radii of curvature that are different from each other.

16 Claims, 29 Drawing Sheets

U.S. PATENT DOCUMENTS

| | | |
|---|---|---|
| 4,063,356 A | 12/1977 | Hepworth et al. |
| 4,069,956 A | 1/1978 | Shearer, Sr. et al. |
| 4,089,112 A | 5/1978 | Richards |
| 4,172,458 A | 10/1979 | Pereyra |
| 4,232,445 A | 11/1980 | Ito et al. |
| 4,233,734 A | 11/1980 | Bies |
| 4,255,881 A | 3/1981 | Fralish |
| 4,322,885 A | 4/1982 | Osada et al. |
| 4,361,958 A | 12/1982 | Gilbert et al. |
| 4,455,690 A | 6/1984 | Homsy |
| 4,467,802 A | 8/1984 | Maslanka et al. |
| 4,679,453 A | 7/1987 | Morita et al. |
| 4,718,419 A | 1/1988 | Okada et al. |
| 4,741,335 A | 5/1988 | Okada et al. |
| 4,775,380 A | 10/1988 | Seedhom et al. |
| 4,946,467 A | 8/1990 | Ohi et al. |
| 5,026,371 A | 6/1991 | Rydell et al. |
| 5,027,674 A | 7/1991 | Nolte et al. |
| 5,029,489 A | 7/1991 | Burmeister et al. |
| 5,084,054 A | 1/1992 | Bencini et al. |
| 5,112,344 A | 5/1992 | Petros et al. |
| 5,152,749 A | 10/1992 | Giesy et al. |
| 5,163,942 A | 11/1992 | Rydell |
| 5,171,233 A | 12/1992 | Amplatz et al. |
| 5,171,314 A | 12/1992 | Dulebohn |
| 5,201,741 A | 4/1993 | Dulebohn |
| 5,269,063 A | 12/1993 | Okada et al. |
| 5,311,858 A | 5/1994 | Adair |
| 5,334,185 A | 8/1994 | Giesy et al. |
| 5,337,736 A | 8/1994 | Reddy |
| 5,342,371 A | 8/1994 | Welter et al. |
| 5,368,595 A | 11/1994 | Lewis |
| 5,397,332 A | 3/1995 | Kammerer et al. |
| 5,447,512 A | 9/1995 | Wilson et al. |
| 5,486,183 A | 1/1996 | Middleman et al. |
| 5,497,553 A | 3/1996 | Chong et al. |
| 5,499,991 A | 3/1996 | Garman et al. |
| 5,501,692 A | 3/1996 | Riza |
| 5,502,896 A | 4/1996 | Chen et al. |
| 5,522,833 A | 6/1996 | Stephens et al. |
| 5,542,948 A | 8/1996 | Weaver et al. |
| 5,562,678 A | 10/1996 | Booker |
| 5,562,688 A | 10/1996 | Riza |
| 5,562,689 A | 10/1996 | Green et al. |
| 5,573,530 A | 11/1996 | Fleury et al. |
| 5,611,515 A | 3/1997 | Benderev et al. |
| 5,628,756 A | 5/1997 | Barker, Jr. et al. |
| 5,640,886 A | 6/1997 | Lai et al. |
| 5,693,072 A | 12/1997 | McIntosh |
| 5,755,728 A | 5/1998 | Maki |
| 5,817,104 A | 10/1998 | Bilitz et al. |
| 5,842,478 A | 12/1998 | Benderev et al. |
| 5,846,248 A | 12/1998 | Chu et al. |
| 5,860,425 A | 1/1999 | Benderev et al. |
| 5,862,596 A | 1/1999 | Chung et al. |
| 5,864,952 A | 2/1999 | Chung et al. |
| 5,899,909 A | 5/1999 | Claren et al. |
| 5,904,692 A | 5/1999 | Steckel et al. |
| 5,910,148 A | 6/1999 | Reimels et al. |
| 5,934,283 A | 8/1999 | Willem et al. |
| 5,935,138 A | 8/1999 | McJames, II et al. |
| 5,961,526 A | 10/1999 | Chu et al. |
| 5,968,008 A | 10/1999 | Grams |
| 5,987,751 A | 11/1999 | Chung et al. |
| 6,006,433 A | 12/1999 | Baltazar |
| 6,030,393 A | 2/2000 | Corlew |
| 6,042,534 A | 3/2000 | Gellman et al. |
| 6,048,354 A | 4/2000 | Lawrence |
| 6,056,688 A | 5/2000 | Benderev et al. |
| 6,059,796 A | 5/2000 | Bilitz et al. |
| 6,074,341 A | 6/2000 | Anderson et al. |
| 6,092,955 A | 7/2000 | Chartrain et al. |
| 6,110,101 A | 8/2000 | Tihon et al. |
| 6,117,162 A | 9/2000 | Schmieding et al. |
| 6,171,315 B1 | 1/2001 | Chu et al. |
| 6,210,416 B1 | 4/2001 | Chu et al. |
| 6,226,873 B1 | 5/2001 | Okumura et al. |
| 6,235,026 B1 | 5/2001 | Smith |
| 6,273,852 B1 | 8/2001 | Lehe et al. |
| 6,312,448 B1 | 11/2001 | Bonutti |
| 6,315,782 B1 | 11/2001 | Chu et al. |
| 6,328,686 B1 | 12/2001 | Kovac |
| 6,346,115 B1 | 2/2002 | Lawrence |
| 6,371,963 B1 | 4/2002 | Nishtala et al. |
| 6,375,661 B2 | 4/2002 | Chu et al. |
| 6,406,423 B1 | 6/2002 | Scetbon et al. |
| 6,409,733 B1 | 6/2002 | Conlon et al. |
| 6,423,080 B1 | 7/2002 | Gellman et al. |
| 6,478,727 B2 | 11/2002 | Scetbon et al. |
| 6,491,703 B1 | 12/2002 | Ulmsten et al. |
| 6,494,887 B1 | 12/2002 | Kaladelfos et al. |
| 6,502,578 B2 | 1/2003 | Raz et al. |
| 6,511,499 B2 | 1/2003 | Schmieding et al. |
| 6,553,674 B1 | 4/2003 | Budrow |
| 6,554,842 B2 | 4/2003 | Heuser et al. |
| 6,596,001 B2 | 7/2003 | Stormby et al. |
| 6,612,977 B2 | 9/2003 | Staskin et al. |
| 6,638,210 B2 | 10/2003 | Berger |
| 6,638,211 B2 | 10/2003 | Suslian et al. |
| 6,638,286 B1 | 10/2003 | Burbank et al. |
| 6,641,524 B2 | 11/2003 | Kovac |
| 6,641,525 B2 | 11/2003 | Rocheleau et al. |
| 6,652,450 B2 | 11/2003 | Neisz et al. |
| 6,652,537 B2 | 11/2003 | Mercereau et al. |
| 6,663,645 B2 | 12/2003 | Nishtala et al. |
| 6,676,668 B2 | 1/2004 | Mercereau et al. |
| 6,685,629 B2 | 2/2004 | Therin |
| 6,689,047 B2 | 2/2004 | Gellman |
| 6,702,827 B1 | 3/2004 | Lund et al. |
| 6,708,410 B2 | 3/2004 | Okada et al. |
| 6,730,097 B2 | 5/2004 | Dennis |
| 6,752,814 B2 | 6/2004 | Gellman et al. |
| 6,789,326 B1 | 9/2004 | Huang et al. |
| 6,802,807 B2 | 10/2004 | Anderson et al. |
| 6,808,486 B1 | 10/2004 | O'Donnell |
| 6,808,487 B2 | 10/2004 | Migliari |
| 6,843,792 B2 | 1/2005 | Nishtala et al. |
| 6,872,227 B2 | 3/2005 | Sump et al. |
| 6,878,134 B2 | 4/2005 | Rogers et al. |
| 6,908,425 B2 | 6/2005 | Luscombe |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,953,428 B2 | 10/2005 | Gellman et al. |
| 6,960,160 B2 | 11/2005 | Browning et al. |
| 6,966,113 B2 | 11/2005 | Fossella |
| 6,971,986 B2 | 12/2005 | Staskin et al. |
| 6,991,597 B2 | 1/2006 | Gellman et al. |
| 7,014,607 B2 | 3/2006 | Gellman |
| 7,025,772 B2 | 4/2006 | Gellman et al. |
| 7,037,255 B2 | 5/2006 | Inman et al. |
| 7,037,307 B2 | 5/2006 | Dennis |
| 7,048,682 B2 | 5/2006 | Neisz et al. |
| 7,052,495 B2 | 5/2006 | Smith |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,087,065 B2 | 8/2006 | Ulmsten et al. |
| 7,094,199 B2 | 8/2006 | Petros et al. |
| 7,101,378 B2 | 9/2006 | Salameh et al. |
| 7,112,171 B2 | 9/2006 | Rocheleau et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin |
| 7,163,506 B2 | 1/2007 | Grise |
| 7,198,597 B2 | 4/2007 | Siegel et al. |
| 7,204,801 B2 | 4/2007 | Grocela |
| 7,204,802 B2 | 4/2007 | De Leval et al. |
| RE39,626 E | 5/2007 | Tihon |
| 7,217,264 B2 | 5/2007 | Gobron et al. |
| 7,226,407 B2 | 6/2007 | Kammerer et al. |
| 7,229,453 B2 | 6/2007 | Anderson et al. |
| 7,235,043 B2 | 6/2007 | Gellman et al. |
| 7,244,259 B2 | 7/2007 | Smith et al. |
| 7,261,723 B2 | 8/2007 | Smith et al. |
| 7,267,645 B2 | 9/2007 | Anderson et al. |

| | | | |
|---|---|---|---|
| 7,285,086 B2 | 10/2007 | Smith et al. |
| 7,288,063 B2 | 10/2007 | Petros et al. |
| 7,291,104 B2 | 11/2007 | Neisz et al. |
| 7,303,525 B2 | 12/2007 | Watschke et al. |
| 7,338,432 B2 | 3/2008 | Valtchev |
| 7,347,812 B2 | 3/2008 | Mellier et al. |
| 7,347,813 B2 | 3/2008 | Claren et al. |
| 7,357,773 B2 | 4/2008 | Watschke |
| 7,407,480 B2 | 8/2008 | Staskin et al. |
| 7,527,588 B2 | 5/2009 | Zaddem et al. |
| 7,691,110 B2 | 4/2010 | Secrest et al. |
| 2001/0049467 A1 | 12/2001 | Lehe et al. |
| 2001/0053916 A1 | 12/2001 | Rioux |
| 2002/0055748 A1 | 5/2002 | Gellman et al. |
| 2002/0077526 A1 | 6/2002 | Kammerer et al. |
| 2002/0091373 A1 | 7/2002 | Berger |
| 2002/0099259 A1 | 7/2002 | Anderson et al. |
| 2002/0099260 A1 | 7/2002 | Suslian et al. |
| 2002/0147382 A1 | 10/2002 | Neisz et al. |
| 2002/0151909 A1 | 10/2002 | Gellman et al. |
| 2002/0156488 A1 | 10/2002 | Gellman et al. |
| 2002/0156489 A1 | 10/2002 | Gellman et al. |
| 2002/0165566 A1 | 11/2002 | Ulmsten |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0036676 A1 | 2/2003 | Scetbon |
| 2003/0045892 A1 | 3/2003 | Kaladelfos |
| 2003/0065402 A1 | 4/2003 | Anderson et al. |
| 2003/0130670 A1 | 7/2003 | Anderson et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0006353 A1 | 1/2004 | Bosley et al. |
| 2004/0015048 A1 | 1/2004 | Neisz et al. |
| 2004/0015057 A1 | 1/2004 | Rocheleau et al. |
| 2004/0039246 A1 | 2/2004 | Gellman et al. |
| 2004/0039453 A1 | 2/2004 | Anderson et al. |
| 2004/0040159 A1 | 3/2004 | Fossella |
| 2004/0068159 A1 | 4/2004 | Neisz et al. |
| 2004/0073234 A1 | 4/2004 | Chu et al. |
| 2004/0087970 A1 | 5/2004 | Chu et al. |
| 2004/0087980 A1 | 5/2004 | Ford et al. |
| 2004/0097974 A1 | 5/2004 | De Leval |
| 2004/0097975 A1 | 5/2004 | Rose |
| 2004/0106845 A1 | 6/2004 | Anderson et al. |
| 2004/0111895 A1 | 6/2004 | Huang |
| 2004/0116774 A1 | 6/2004 | Migliari |
| 2004/0116944 A1 | 6/2004 | Chu et al. |
| 2004/0133217 A1 | 7/2004 | Watschke |
| 2004/0144395 A1 | 7/2004 | Evans et al. |
| 2004/0225181 A1 | 11/2004 | Chu et al. |
| 2004/0225301 A1 | 11/2004 | Roop et al. |
| 2004/0230206 A1 | 11/2004 | Gellman et al. |
| 2004/0230207 A1 | 11/2004 | Gellman et al. |
| 2004/0249473 A1 | 12/2004 | Delorme et al. |
| 2004/0267088 A1 | 12/2004 | Kammerer |
| 2005/0021086 A1 | 1/2005 | De Leval |
| 2005/0028380 A1 | 2/2005 | Fossella |
| 2005/0033365 A1 | 2/2005 | Courage |
| 2005/0043580 A1 | 2/2005 | Watschke et al. |
| 2005/0070829 A1 | 3/2005 | Therin et al. |
| 2005/0075660 A1 | 4/2005 | Chu et al. |
| 2005/0085831 A1 | 4/2005 | Rioux |
| 2005/0090706 A1 | 4/2005 | Gellman et al. |
| 2005/0090841 A1 | 4/2005 | Morrison |
| 2005/0101834 A1 | 5/2005 | Merade |
| 2005/0101973 A1 | 5/2005 | Smith et al. |
| 2005/0107660 A1 | 5/2005 | Valtchev |
| 2005/0113845 A1 | 5/2005 | Griego et al. |
| 2005/0131391 A1 | 6/2005 | Chu |
| 2005/0131392 A1 | 6/2005 | Chu et al. |
| 2005/0131393 A1 | 6/2005 | Chu et al. |
| 2005/0143618 A1 | 6/2005 | Anderson et al. |
| 2005/0148813 A1 | 7/2005 | Claren et al. |
| 2005/0177022 A1 | 8/2005 | Chu et al. |
| 2005/0240076 A1 | 10/2005 | Neisz et al. |
| 2005/0256366 A1 | 11/2005 | Chu |
| 2005/0261545 A1 | 11/2005 | Gellman et al. |
| 2005/0277807 A1 | 12/2005 | MacLean et al. |
| 2006/0015001 A1 | 1/2006 | Staskin et al. |
| 2006/0015069 A1 | 1/2006 | Evans et al. |
| 2006/0025649 A1 | 2/2006 | Smith et al. |
| 2006/0058574 A1 | 3/2006 | Priewe et al. |
| 2006/0058575 A1 | 3/2006 | Zaddem et al. |
| 2006/0059693 A1 | 3/2006 | Fossella |
| 2006/0059695 A1 | 3/2006 | Levine et al. |
| 2006/0063968 A1 | 3/2006 | Anderson et al. |
| 2006/0089524 A1 | 4/2006 | Chu |
| 2006/0089525 A1 | 4/2006 | Mamo et al. |
| 2006/0106277 A1 | 5/2006 | Romero Maroto |
| 2006/0122457 A1 | 6/2006 | Kovac et al. |
| 2006/0130848 A1 | 6/2006 | Carey |
| 2006/0134159 A1 | 6/2006 | Nicita |
| 2006/0173237 A1 | 8/2006 | Jacquetin |
| 2006/0173471 A1 | 8/2006 | Carr, Jr. et al. |
| 2006/0173864 A1 | 8/2006 | Evans et al. |
| 2006/0183966 A1 | 8/2006 | Neisz et al. |
| 2006/0195007 A1 | 8/2006 | Anderson et al. |
| 2006/0195010 A1 | 8/2006 | Arnal et al. |
| 2006/0195011 A1 | 8/2006 | Arnal et al. |
| 2006/0195013 A1 | 8/2006 | Gellman et al. |
| 2006/0199994 A1 | 9/2006 | Inman et al. |
| 2006/0205995 A1 | 9/2006 | Browning |
| 2006/0205998 A1 | 9/2006 | Li et al. |
| 2006/0229493 A1 | 10/2006 | Weiser et al. |
| 2006/0229596 A1 | 10/2006 | Weiser et al. |
| 2006/0258897 A1 | 11/2006 | Petros et al. |
| 2006/0258898 A1 | 11/2006 | Montpetit et al. |
| 2006/0287571 A1 | 12/2006 | Gozzi et al. |
| 2007/0010830 A1 | 1/2007 | Gellman et al. |
| 2007/0015957 A1 | 1/2007 | Li |
| 2007/0021649 A1 | 1/2007 | Nowlin et al. |
| 2007/0021650 A1 | 1/2007 | Rocheleau et al. |
| 2007/0021686 A1 | 1/2007 | Gellman et al. |
| 2007/0032695 A1 | 2/2007 | Weiser |
| 2007/0038017 A1 | 2/2007 | Chu |
| 2007/0038018 A1 | 2/2007 | Chu |
| 2007/0043336 A1 | 2/2007 | Griffin et al. |
| 2007/0049790 A1 | 3/2007 | Wagner et al. |
| 2007/0055095 A1 | 3/2007 | Chu et al. |
| 2007/0060788 A1 | 3/2007 | Gellman |
| 2007/0062541 A1 | 3/2007 | Zhou et al. |
| 2007/0068538 A1 | 3/2007 | Anderson et al. |
| 2007/0089750 A1 | 4/2007 | Astani et al. |
| 2007/0089751 A1 | 4/2007 | Astani et al. |
| 2007/0123746 A1 | 5/2007 | MacLean |
| 2007/0142698 A1 | 6/2007 | Bourne et al. |
| 2007/0156012 A1 | 7/2007 | Tracey et al. |
| 2007/0161849 A1 | 7/2007 | Goldberg |
| 2007/0203429 A1 | 8/2007 | Ziv |
| 2007/0225546 A1 | 9/2007 | Anderson et al. |
| 2007/0299299 A1 | 12/2007 | Rosenblatt |
| 2007/0299300 A1 | 12/2007 | Smith et al. |
| 2008/0009665 A1 | 1/2008 | Merade et al. |
| 2008/0009667 A1 | 1/2008 | Longhini et al. |
| 2008/0039678 A1 | 2/2008 | Montpetit et al. |
| 2008/0045782 A1 | 2/2008 | Jimenez |
| 2009/0318752 A1 | 12/2009 | Evans et al. |
| 2010/0010501 A2 | 1/2010 | Meade et al. |
| 2010/0217069 A1 | 8/2010 | Meade et al. |
| 2010/0241105 A1 | 9/2010 | Meade et al. |

FOREIGN PATENT DOCUMENTS

| | | |
|---|---|---|
| DE | 4220283 A1 | 12/1993 |
| DE | 4334419 A1 | 4/1995 |
| DE | 19544162 C1 | 4/1997 |
| DE | 10138950 A1 | 2/2003 |
| DE | 10245076 A1 | 4/2004 |
| EP | 0537769 A1 | 4/1993 |
| EP | 0557964 A1 | 9/1993 |
| EP | 0598976 A2 | 6/1994 |
| EP | 0619984 A1 | 10/1994 |
| EP | 0648474 A1 | 4/1995 |
| EP | 0668056 A1 | 8/1995 |

| | | | |
|---|---|---|---|
| EP | 0692225 A2 | 1/1996 |
| EP | 0774240 A1 | 5/1997 |
| EP | 0913162 A1 | 5/1999 |
| EP | 0941712 A1 | 9/1999 |
| EP | 0983033 B1 | 3/2000 |
| EP | 1018980 B1 | 7/2000 |
| EP | 1093758 | 4/2001 |
| EP | 1159920 A2 | 12/2001 |
| EP | 1239793 B1 | 9/2002 |
| EP | 1239795 B1 | 9/2002 |
| EP | 1342450 A1 | 9/2003 |
| EP | 1342454 A1 | 9/2003 |
| EP | 1399082 B1 | 3/2004 |
| EP | 1417934 A2 | 5/2004 |
| EP | 1487377 A1 | 12/2004 |
| EP | 1534154 | 6/2005 |
| EP | 1549245 B1 | 7/2005 |
| EP | 1600118 A1 | 11/2005 |
| EP | 1609439 A1 | 12/2005 |
| EP | 1610714 A2 | 1/2006 |
| EP | 1688105 A2 | 8/2006 |
| FR | 2712177 A1 | 5/1995 |
| FR | 2785521 | 5/2000 |
| FR | 0102120 | 1/2002 |
| FR | 2852817 A1 | 10/2004 |
| FR | 2859624 A1 | 3/2005 |
| FR | 2859901 A1 | 3/2005 |
| GB | 2382993 B | 6/2003 |
| JP | 03070567 A | 3/1991 |
| JP | 11221221 A | 8/1999 |
| JP | 2002143290 A | 5/2002 |
| SE | 503271 C2 | 4/1996 |
| WO | 9003766 A1 | 4/1990 |
| WO | 9208412 A1 | 5/1992 |
| WO | 9310731 A1 | 6/1993 |
| WO | 9315690 A2 | 8/1993 |
| WO | 9603091 A1 | 2/1996 |
| WO | 9606597 A1 | 3/1996 |
| WO | 9607355 A1 | 3/1996 |
| WO | 9608587 A1 | 3/1996 |
| WO | 9640307 A1 | 12/1996 |
| WO | 9713465 A1 | 4/1997 |
| WO | 9743982 A1 | 11/1997 |
| WO | 9831301 A1 | 7/1998 |
| WO | 9835632 A1 | 8/1998 |
| WO | 9922873 A1 | 5/1999 |
| WO | 9934744 A1 | 7/1999 |
| WO | 0027304 A1 | 5/2000 |
| WO | 0040158 A2 | 7/2000 |
| WO | 0064370 A1 | 11/2000 |
| WO | 0074594 A1 | 12/2000 |
| WO | 0074613 A1 | 12/2000 |
| WO | 0106951 A1 | 2/2001 |
| WO | 0130246 | 5/2001 |
| WO | 0147438 A1 | 7/2001 |
| WO | 0180774 A1 | 11/2001 |
| WO | 0193656 A2 | 12/2001 |
| WO | 0202031 A1 | 1/2002 |
| WO | 0219945 A2 | 3/2002 |
| WO | 0228312 A1 | 4/2002 |
| WO | 0232284 A2 | 4/2002 |
| WO | 0238079 A2 | 5/2002 |
| WO | 0239890 A2 | 5/2002 |
| WO | 02058562 A1 | 8/2002 |
| WO | 02058565 A2 | 8/2002 |
| WO | 02065923 A1 | 8/2002 |
| WO | 02069781 A2 | 9/2002 |
| WO | 02071931 A1 | 9/2002 |
| WO | 02078548 A1 | 10/2002 |
| WO | 02098322 A1 | 12/2002 |
| WO | 03002027 A1 | 1/2003 |
| WO | 03028585 A2 | 4/2003 |
| WO | 03037215 A2 | 5/2003 |
| WO | 03053252 A1 | 7/2003 |
| WO | 03068107 A1 | 8/2003 |
| WO | 03073960 A1 | 9/2003 |
| WO | 03086205 A2 | 10/2003 |
| WO | 03096929 A1 | 11/2003 |
| WO | 03096930 A1 | 11/2003 |
| WO | 03101344 A1 | 12/2003 |
| WO | 2004004600 A1 | 1/2004 |
| WO | WO-2004008977 A1 | 1/2004 |
| WO | 2004012579 A2 | 2/2004 |
| WO | 2004012626 A1 | 2/2004 |
| WO | 2004016196 A2 | 2/2004 |
| WO | 2004017862 A2 | 3/2004 |
| WO | 2004034912 A1 | 4/2004 |
| WO | 2004056273 A1 | 7/2004 |
| WO | 2004091442 A2 | 10/2004 |
| WO | 2004098461 A2 | 11/2004 |
| WO | 2005037132 A2 | 4/2005 |
| WO | 2005087153 A2 | 9/2005 |
| WO | 2005094741 A1 | 10/2005 |
| WO | 2005110273 A1 | 11/2005 |
| WO | 2005110274 A1 | 11/2005 |
| WO | 2005112842 A1 | 12/2005 |
| WO | 2005122954 A1 | 12/2005 |
| WO | 2006045042 A1 | 4/2006 |
| WO | 2006046950 A1 | 5/2006 |
| WO | 2006081545 | 8/2006 |
| WO | 2006084165 A2 | 8/2006 |
| WO | 2006084166 A2 | 8/2006 |
| WO | 2006108964 A2 | 10/2006 |
| WO | WO 2007/149348 | 12/2007 |

OTHER PUBLICATIONS

Feb. 4, 2008 International Preliminary Report on Patentability from application PCT/US2006/030370.

BARD (Article), "Avaulta• BioSynthetic Support System," http://www.crbard.com/news/innovations/Avaulta.cfm (2007).

BARD (Article), "Avault• Bio-Synthetic Support System 'Anterior and Posterior Posterior Pelvic Floor Defect Repair with the Avaulta• Bio-synthetic Support system,'" http://www.bardmdu.com/products/loadProduct.aspx? prodID=280&bUnitID=3 (2007).

BARD (Article), "PelviLace® TO Trans-Obturator BioUrethral Support System," http://www.bardurological.com/products/loadproduct.aspx?prodID=277 (2008).

BARD Photo Library, Uretex® Mesh in the Anatomy—printed Jul. 12, 2006 <http://www.bardurological.com/products/product_photoLibrary.aspx?prodID=185&photoID=270>.

BARD Photo Library, Hook Introducer 2 printed Jul. 12, 2006 <http://www.bardurological.com/products/product_photoLibrary.aspx?prodID=186&photoID=344>.

BARD Photo Library, Hook Introducer printed Jul. 12, 2006 http://www.bardurological.com/products/product_photoLibrary.aspx?prodID=186&photoID=343.

BARD Photo Library, Pelvic Diagram 1 (photo id 282) printed Jul. 12, 2006 http://www.bardurological.com/products/product_photoLibrary.aspx?prodID=186&photoID=282.

BARD Photo Library, Pelvic Diagram 2 (photo id 283) printed Jul. 12, 2006 http://www.bardurological.com/products/product_photoLibrary.aspx?prodID=186&photoID=283.

BARD Photo Library, Pelvic Diagram 3 (photo id 284) printed Jul. 12, 2006 http://www.bardurological.com/products/product_photoLibrary.aspx?prodID=186&photoID=284.

BARD Photo Library, Pelvic Diagram 4 (photo id 285) printed Jul. 12, 2006 http://www.bardurological.com/products/product_photoLibrary.aspx?prodID=186&photoID=285.

BARD Photo Library, Surgical Technique (photo id 336) printed Jul. 12, 2006 http://www.bardurological.com/products/product_photoLibrary.aspx?prodID=186&photoID=336.

BARD Photo Library, Surgical Techniques (photo id 337) printed on Jul. 12, 2006 http://www.bardurological.com/products/product_photoLibrary.aspx?prodID=186&photoID=337.

BARD Photo Library, Surgical Techniques (photo id 338) printed Jul. 12, 2006 http://www.bardurological.com/products/product_photoLibrary.aspx?prodID=186&photoID=338.

BARD Photo Library, Surgical Techniques (photo id 339) printed Jul. 12, 2006 http://www.bardurological.com/products/product_photoLibrary.aspx?prodID=186&photoID=339.

BARD Photo Library, Surgical Techniques (photo id 340) printed Jul. 12, 2006 http://www.bardurological.com/products/product_photoLibrary.aspx?prodID=186&photoID=340.

BARD Photo Library, Surgical Techniques (photo id 341) printed Jul. 12, 2006 http://www.bardurological.com/products/product_photoLibrary.aspx?prodID=186&photoID=341.

BARD Photo Library, Surgical Techniques (photo id 345) printed Jul. 12, 2006 http://www.bardurological.com/products/product_photoLibrary.aspx?prodID=186&photoID=345.

BARD Photo Library, Uretex T.O. Transobturator Urethral Support System printed Jul. 12, 2006 <http://www.bardurological.com/products/product_photoLibrary.aspx?productID=186&photoID=266>.

BARD Photo Library, Uretex® to Trans-Obturator Urethral Support System dated Oct. 23, 2008<http://www. bardurological.com/products/product_photoLibrary.aspx?prodID=186&photoID=204&bUnitID=2>.

BARD Photo Library, Urethral Mesh printed Jul. 12, 2006 <http://www.bardurological.com/products/product_photoLibrary.aspx?prodID=185&photoID=271>.

Burch, John C., "Urethrovaginal fixation to Cooper's ligament for correction of stress incontinence, cystocele, and prolapse," Am. J. Obst. & Gyne, 281-290 (1961).

Choe, JM, "Preventing urethral obstruction using the 6-point fixation and weight-adjusted spacing nomogram during sling surgery," Int Urogynecol J Pelvic Floor Dysfunct, 2001;12(2):122-8.

Collinet, P., et al., "Cure de cystocele par plastron vaginal," J Gynecol Obstet Biol Reprod, 29:197-201 (2000).

Cosson, M., et al., "Cure of cystocele with vaginal patch," Prog Urol. Apr. 2001;11(2):340-6.

Cosson, M., et al., "The vaginal patch plastron for vaginal cure of cystocele. Preliminary results for 47 patients," Eur J Obstet Gynecol Reprod Giol. Mar. 2001;95(1):73-80.

Cosson, Michel, et al., "Cure de cystocele par plastron vaginal," Progres en Urologie, 11:340-346 (2001).

Cruikshank, Stephen H., et al., "Anterior vaginal wall culdeplasty at vaginal hysterectomy to prevent posthysterectomy anterior vaginal wall prolapse," Am. J. Obstet. Gynecol., 1863-1872 (1996).

De Leval J., "Novel surgical technique for the treatment of female stress urinary incontinence: transobturator vaginal tape inside-out," Eur Urol. Dec. 2003;44(6):724-30.

DeLorme, E., "Transobturator urethral suspension: mini-invasive procedure in the treatment of stress urinary incontinence in women," Prog Urol. Dec. 2001;11(6):1306-13.

DeLorme, E., et al., "Transobturator tape (Uratape). A new minimally invasive method in the treatment of urinary incontinence in women," Prog Urol. Sep. 2003;13(4):656-9.

Di Benedetto, V., et al., "Transurethral Puncture of Ureterocele Associated With Single Collecting System in Neonates," J. Ped. Surg., 32: 1325-1327, 1997.

Dmochowski et al., "Biocompatibility Assessment of Synthetic Sling Materials for Female Stress Urinary Incontinence," The Journal of Urology, vol. 178, Issue 4, pp. 1171-1181, Oct. 2007.

Dmochowski et al., "Erosion of Woven Polyester Pubovaginal Sling," The Journal of Urology, vol. 162, Issue 6, pp. 2070-2072, Dec. 1999.

Dmochowski, R., et al., "The Protegen Sling for the Treatment of Female Stress Urinary Incontinence," J. Urol., http://home.satx.rr.com/sgsu/usurg/protegen.html (1997).

Eglin, G., et al., "Transobturator subvesical mesh. Tolerance and short-term results of a 103 case continuous series," Gynecology Obstetrique & Fertilite, Jan. 2003;31(1):14-19(6).

EP 06789465.9 filed Aug. 3, 2006 Search Report dated Apr. 28, 2010.
EP 06800736.8 filed Aug. 3, 2006 Search Report dated Apr. 26, 2010.
EP 06824802.0 filed Aug. 3, 2006 Search Report dated Dec. 13, 2010.
EP 06846828.9 filed Dec. 28, 2006 Office Action dated May 18, 2010.
EP 06846828.9 filed Dec. 28, 2006 Search Report dated Apr. 26, 2010.

Glowacki, CA, et al., "Bone anchors in urogynecology," Clin Obstet Gynecol, Sep. 2000;43(3):659-69, Review.

Gomelsky, Alex, et al., "Biocompatibility Assessment of Synthetic Sling Materials for Female Stress Urinary Incontinence," The Journal of Urology, Oct. 2007, vol. 178, pp. 1171-1181.

Image, <http://www.ivstunneller.com/images/anterior-procedure.jpg>printed on Jul. 10, 2006.

Iosif, S., et al., "Urodynamic studies of women with prolapse and stress incontinence before and after surgical repair," Urodynamics Studies, 101:1433-1442 (1979).

U.S. Appl. No. 11/993,003, filed Jan. 22, 2008 Advisory Action dated Feb. 8, 2011.
U.S. Appl. No. 11/993,003, filed Jan. 22, 2008 Final Office Action dated Dec. 10, 2010.
U.S. Appl. No. 11/993,003, filed Jan. 22, 2008 Non-Final Office Action dated Jul. 14, 2010.
U.S. Appl. No. 12/159,589, filed Aug. 15, 2008 Non-Final Office Action dated Dec. 10, 2010.
U.S. Appl. No. 12/159,589, filed Aug. 15, 2008 Non-Final Office Action dated Jul. 12, 2010.

Wall, LL, et al. Use of a pedicled rectus abdominus muscle flap sling in the treatment of complicated stress urinary incontinence. Am J Obstet Gynecol. Dec. 1996;175(6):1460-4; Discussion 1464-6.

Walters, Mark D., et al., "Anterior vaginal wall prolapse: Innovative surgical approaches," Cleveland Clinic Journal of Medicine, Dec. 2005, 72:4 S20-S27.

Yan, A., et al, "Cystocele repair by a synthetic vaginal mesh secured anteriorly through the obturator foramen," Eur J Obstet Gynecol Reprod Biol, Jul. 15, 2004;115(1):90-4.

Zimmern, Philippe, et al., "A prospective evaluation of four-corner bladder neck suspension for grade II/III cystocele repair," Urodynamics Soc. Symp. Abstracts, p. 231 (1990).

Jacquetin B., "Bladder suspension exclusively through the vagina: at last!" J Gynecol Obstet Biol Reprod 1991;20 (8):1143-4, Paris.

Jacquetin B., "Genital prolapses. Diagnosis," Rev Prat. Sep. 15, 2001;51(14):1609-16.

Jacquetin B., "Use of "TVT" in surgery for female urinary incontinence," J Gynecol Obstet Biol Reprod, May 2000;29(3):242-7.

Johnson & Johnson (Article), "Gynecare Prolift Systems: 'You Know Where You Want to Go . . . GPS for Pelvic Floor Repair,'" <http://www.jnjgateway.com/home.jhtml?loc=USENG&page=viewContent&contentId=09008b98>8102f39b&parentId=09008b988102f39b (2006).

Johnson & Johnson Gateway®, "Optimal technique for access to anatomic landmarks," <http://www.jnjgateway.com/home.jhtml?loc=USENG&page=viewContent&contentID=090> (2005).

Johnson & Johnson Gateway®: Gynecare Prolift Innovative Design, http://www.jnjgateway.com/home.jhtml?loc=USENG&page=viewContent&contentID=090 (2005).

Johnson & Johnson Gateway®: Gynecare TVT Abdominal Approach, <http://www.jnjgateway.com/home.jhtml?loc=USENG&page=vieewContent&contentID=090> (2005).

Johnson & Johnson Gateway®: Gynecare TVT Obturator System, "Tension-Free Support for Incontinence" <http://www.jnjgateway.com/home.jhtml?loc=USENG&page=viewContent&contentID=090> (2005).

Johnson & Johnson Gateway®: Vaginal Approach, <http://www.jnjgateway.com/home.jhtml?loc=USENG&page=viewContent&contentID=090> (2005).

Karmarkar, Santoshi J., et al., "The 3-loop technique: A reliable technique for anterior pubic fixation in bladder exstrophy," The Journal of Urology, Sep. 1995 vol. 154, 1173-1176.

Kobashi, Kathleen C., et al., "Erosion of Woven Polyester Pubovaginal Sling," The Journal of Urology, Dec. 1999, vol. 162, pp. 2070-2072.

MedlinePlus Medical Encyclopedia, "Female urinary tract," http://www.nlm.nih.gov/medlineplus/ency/imagepages/1122.htm (2004).

Moore, Robert D., "Transobturator Approach for Cystocele Repair With Anterior Wall Mesh," <http://www.obgyn.net/hysterectomy-alternatives/hysterectomy-alternatives.asp>? page=urogyn/articles/moore_cystocele (2006).

Mubiayi N., et al., "Surgical cure of stress urinary incontinence with vaginal tissue sling: technique, results, indications," Prog Urol. Feb. 2002;12(1):60-9.

Nguyen, JK, "Current concepts in the diagnosis and surgical repair of anterior vaginal prolapse due to paravaginal defects," Obstet Gynecol Surv, Apr. 2001;56(4):239-46.

Nickel, RF, et al, "Evaluation of a transpelvic sling procedure with and without colposuspension for treatment of female dogs with refractory urethral sphincter mechanism incompetence." Vet Surg. Mar.-Apr. 1998;27(2):94-104.

Okoshi, Takafumi, et al., "Long-term Results of a New Antithrombogenic Cardiac Wall Substitute," Trans Am Soc. Artif Intern Organs, XXXV:391-395 (1989).

PCT/AU2000/001298 filed Oct. 20, 2000 International Preliminary Examination Report dated Jan. 29, 2002.

PCT/AU2000/001298 filed Oct. 20, 2000 Search Report dated Jan. 3, 2001.

PCT/US2003/013113 dated Apr. 28, 2003 International Preliminary Examination Report dated Oct. 14, 2004.

PCT/US2003/013113 dated Apr. 28, 2003 Seach Report dated Oct. 15, 2003.

PCT/US2006/030369 filed Aug. 3, 2006 International Preliminary Report on Patentability dated Mar. 31, 2009.

PCT/US2006/030369 filed Aug. 3, 2006 Search Report dated Aug. 12, 2008.

PCT/US2006/030369 filed Aug. 3, 2006 Written Opinion dated Aug. 12, 2008.

PCT/US2006/030370 filed Aug. 3, 2006 Written Opinion dated Jul. 20, 2007.

PCT/US2006/030581 filed Aug. 3, 2006 International Preliminary Report on Patentability dated Mar. 17, 2009.

PCT/US2006/030581 filed Aug. 3, 2006 Search Report dated Jul. 7, 2008.

PCT/US2006/030581 filed Aug. 3, 2006 Written Opinion dated Jul. 7, 2008.

PCT/US2006/062639 filed Dec. 28, 2006 International Preliminary Report on Patentability dated Oct. 7, 2008.

PCT/US2006/062639 filed Dec. 28, 2006 Search Report dated Oct. 1, 2007.

PCT/US2006/062639 filed Dec. 28, 2006 Written Opinion dated Oct. 1, 2007.

PCT/US2007/006461 filed on Mar. 15, 2007 International Preliminary Report on Patentability dated Sep. 16, 2008.

PCT/US2007/006461 filed on Mar. 15, 2007 Search Report dated May 22, 2008.

PCT/US2007/006461 filed on Mar. 15, 2007 Written Opinion dated May 22, 2008.

Pelosi, Ma, et al., "The transobturator sling: newest tension-free suburethral sling for treatment of stress urinary incontinence," Surg Technol Int. 2004;13:173-9. Review.

Petros, Peter E. Papa, "Ambulatory surgery for urinary incontinence and vaginal prolapse," Med. J. of Australia, 161:171-172 (1994).

Scotti, RJ, et al., "Paravaginal repair of lateral vaginal wall defects by fixation to the ischial periosteum and obturator membrane," Am J Obstet Gynecol. Dec. 1998;179(6 Pt 1):1436-45.

Silver, Richard I., et al., "Staged closure of the pelvis in cloacal exstrophy: first description of a new approach," The Journal of Urology, Jan. 1999, vol. 161, pp. 263-266.

Sussman, J.S., et al., "A Comparison of Methods of Repairing the Symphysis Pubis in Bladder Exstrophy by Tensile Testing," Brit. J. Urol., 79: 979-984, 1997.

BARD (Article), "Uretex® TO—Trans-Obturator Urethral Support System 'Not all Mesh is created equal,'" Copyright 1997-2004, <http://www.bardurologcial.com/products/loadproductaspx?prodID=186>.

BARD Photo Library "Uretex® Mesh," printed Jul. 12, 2006; http://www.bardurological.com/products/product_photoLibrary.aspx?prodID=185&photoID=269.

BARD Photo Library, Avaulta™ "Posterior BioSynthetic Support System", Copyright 1997-2008; printed Oct. 23, 2008; http://www.bardurological.com/products/product_photolibrary.aspx?prodID=281&photoID=326>.

BARD, "Avaulta™ Anterior BioSynthectic Support System," Copyright 2006-2011, http://www.bardnordic.com/main/product.asp?.sectionTypeID=2&sectionID=6&productID=247.

BARD, "Uretex® Self-Anchoring Urethral Support System—FAQ," printed Jul. 12, 2006; <http://www.bardurological.com/products/product_faq.aspx?prodID=185>.

Image, www.obgyn.neUurogyn/articles/moore_cystocele, printed Jul. 10, 2006 and Mar. 10, 2011, <http://www.obgyn.neUurogyn/articles/moore_cystocele>.

Karlovsky, Matthew E., et al., "Surgical Treatment of Stress Urinary Incontinence", Journal of Urology, 2003.

Miklos et al., Laparoscopic Urogynecology Center of Atlanta—Dr. Miklos & Dr. Moore, "Laparoscopic and Minimally Invasive Procedures, 'Tension Free Vaginal Tape (TVT) Sling'" printed Jul. 12, 2006; <http://www.urogynecologychannel.net/lap_proc12.php>.

Miklos et al., Vaginal prolapse relaxation and enterocele repair, printed Jul. 12, 2006; http://www.urogynecologychannel.net/prolapse6.php.

Miklos et al., Vaginal prolapse relaxation, posterior vaginal wall prolapse, printed Jul. 12, 2006; http://www.urogynecologychannel.net/prolapse3.php.

Miklos et al., Vaginal prolapse relaxation, uterine prolapse, printed Jul. 12, 2006; <http://www.urogynecologychannel.net/prolapse4.php>.

Miklos et al., Vaginal prolapse relaxation, uterosacral ligaments, printed Jul. 12, 2006; http://www.urogynecologychannel>.net/prolapse2a.php.

Miklos et al., Vaginal prolapse relaxation, vaginal vault prolapse, printed Jul. 12, 2006; <http://www.urogynecologychannel.net/prolapse5.php>.

Miklos et al., Vaginal relaxation, vaginal prolapse relaxaton, enterocele repair, Types of Vaginal Prolapse, printed on Jul. 12, 2006, http://www.urogyneocologychannel.net/prolapse.php?id=Prolapse.

Netterimages.com, "Cystocele, Urethrocele," Image No. 5192, printed Jul. 24, 2006; <http://ww.netterimages.com/images/vpv/000/000/005/5192-05>....

Netterimages.com, "Rectocele, Enterocele," Image No. 5193, printed Jul. 24, 2006; <http://www.netterimages.com/image/5193.htm>.

Shands Healthcare, "Bladder neck is elevated by stitching it and the urethra to anterior pubic bone," Copyright 1997-2011, printed Nov. 3, 2010,<http://www.shands.org/health/imagepages/17202.htm>.

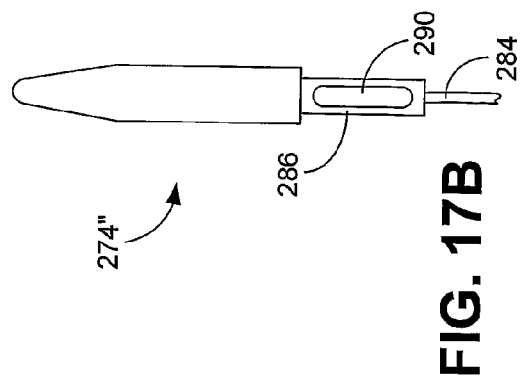
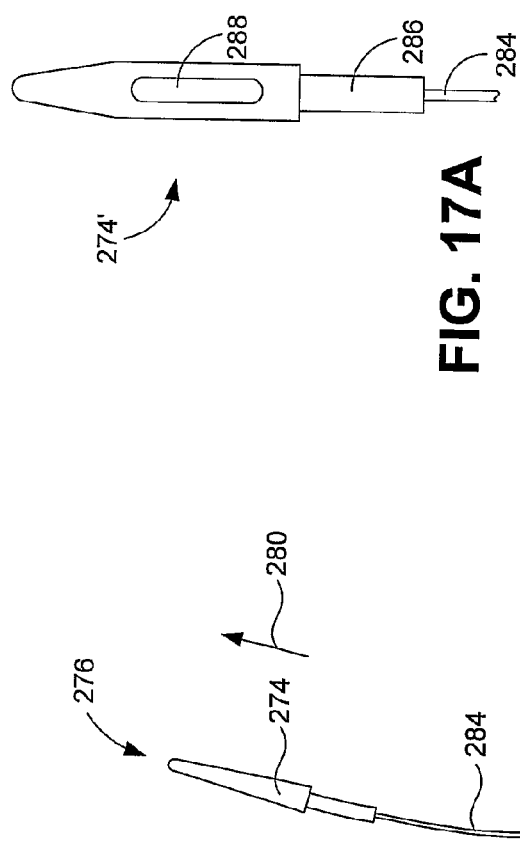
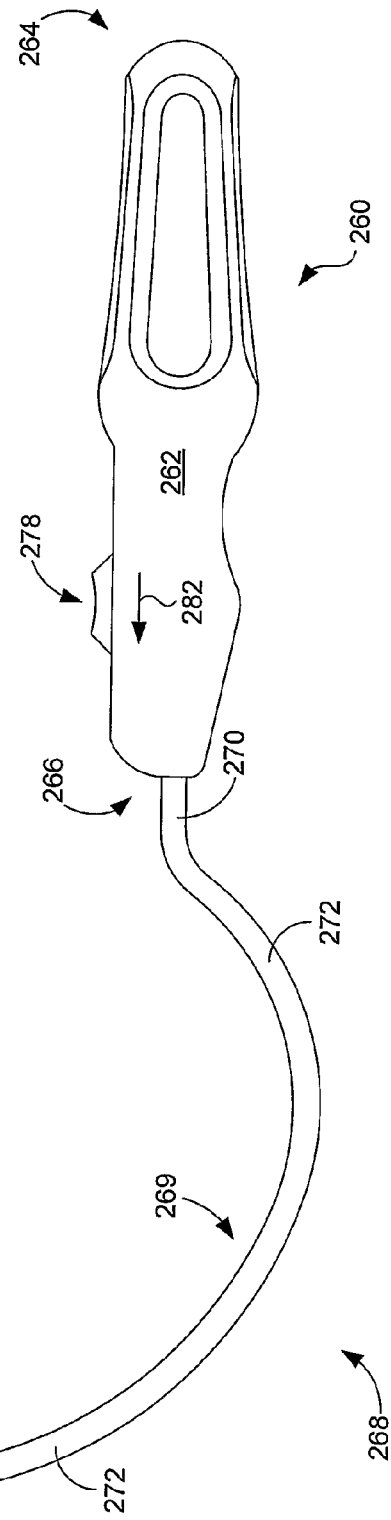

PELVIC IMPLANT SYSTEMS AND METHODS

CROSS-REFERENCE TO RELATED APPLICATION

This application a United States national stage application under 35 U.S.C. §371 of International Patent Application No. PCT/US2006/030370, filed Aug. 3, 2006, which claims the benefit, under 35 U.S.C. §119(e), to U.S. Provisional Application No. 60/705,569, filed Aug. 4, 2005, U.S. Provisional Application No. 60/705,624, filed Aug. 4, 2005, and U.S. Provisional Application No. 60/810,065, filed Jun. 1, 2006 each of which is incorporated by reference into this application as if fully set forth herein.

BACKGROUND

Pelvic implants are used to treat various ailments. For example, pelvic implants are used to perform prolapse repair and to treat urinary incontinence. Such implants are often composed of a knitted mesh that, once implanted, enables the ingrowth of soft tissue to fix the implant in place. Although various implants have been proposed, many do not adequately conform to the anatomy of the patient.

Positioning an implant within the human body, such as within the pelvis, can be challenging due to the anatomy of the body and the placement of the implant that may be required to treat a given ailment. For instance, the treatment of rectocele may require accessing the vaginal vault from a position deep within the pelvis so as to form a passage in which a portion, such as an anchoring arm, of the implant can be placed. Given the configuration and dimensions of the human pelvis and its organs, it can be difficult to navigate a needle through such a tortuous path without causing damage to or otherwise disrupting the tissues of the pelvis, such as the pelvic floor muscles.

BRIEF DESCRIPTION OF THE DRAWINGS

The disclosed systems and methods can be better understood with reference to the following drawings. The components in the drawings are not necessarily to scale.

FIG. 16 is a further side view of the posterior introducer of FIG. 15 illustrating extension of a tip member of the introducer.

FIG. 17A is a side view of a first embodiment of a tip member that can be provided on the posterior introducer of FIGS. 15 and 16.

FIG. 17B is a side view of a second embodiment of a tip member that can be provided on the posterior introducer of FIGS. 15 and 16.

DETAILED DESCRIPTION

Disclosed herein are pelvic implant systems and methods for the treatment of pelvic ailments. More particularly, described are prolapse repair implants, introducers for implanting the implants, and methods for implanting the implants. Although prolapse repair is described with specificity in the following, it will be understood that the systems and/or methods of the present disclosure may be relevant to the treatment of other pelvic ailments, such as urinary incontinence. Moreover, although specific embodiments are presented in the following, it is to be appreciated that those embodiments are mere example implementations of the disclosed systems and methods and other embodiments are possible. All such embodiments are intended to fall within the scope of this disclosure.

FIGS. 1-4 illustrate embodiments of implants suitable for use in treating prolapse. The implants each have a body portion and arms that extend from the body portion. The body portion can be positioned adjacent an organ to be supported, such as the bladder, rectum, uterus, or urethra. Generally speaking, the implants are formed from a flexible material. The implant material can be a synthetic material, a natural material, or a combination of both synthetic and natural materials. The natural material can comprise, for example, a porcine dermal collagen material. The synthetic material can comprise a polymeric mesh, for example, polypropylene mesh. In some embodiments, the synthetic material comprises knitted monofilament, polypropylene mesh having multidirectional elasticity that provides long-term reinforcement of pelvic support structures. Irrespective of the material used to construct the implants, the implants are highly flexible yet have the strength needed for tension-free fixation of the implant.

Figure 1:
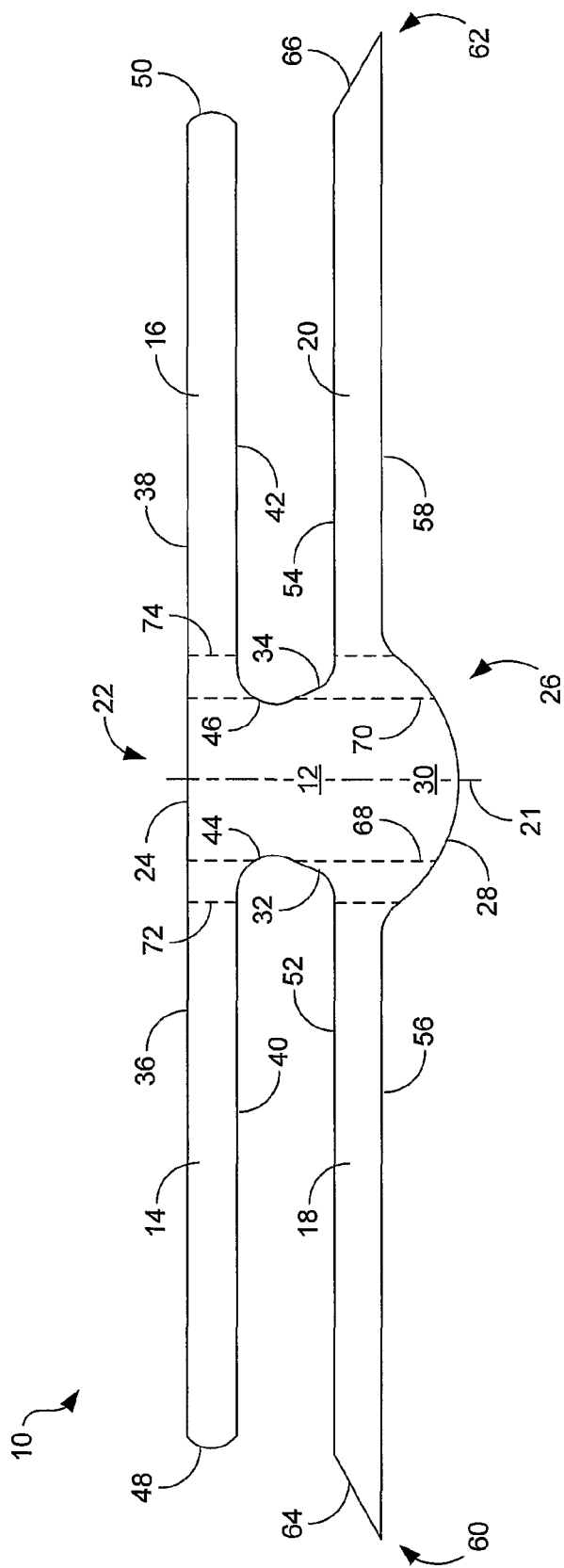
FIG. 1 is a top view of an embodiment of an anterior implant suitable for use in treating cystocele.
Figure 2:
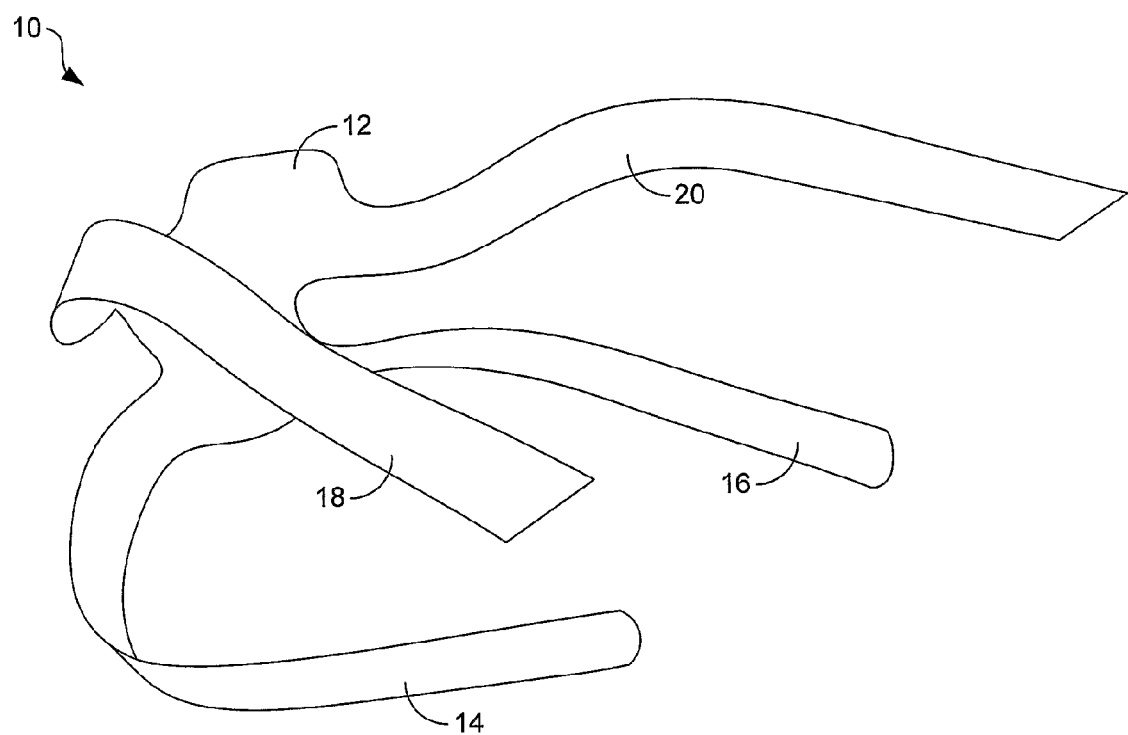
FIG. 2 is a perspective view of the anterior implant of FIG. 1.

FIGS. 1 and 2 illustrate an embodiment of an anterior implant 10, which may be used to treat cystocele. As indicated in FIG. 1, the implant 10 generally comprises a body portion 12, two front arms 14 and 16, and two rear arms 18 and 20. The body portion 12 defines a central axis 21 about which the implant 10 is substantially symmetric and generally comprises a front side 22 defined by front edge 24 and a rear side 26 defined by a rear edge 28. In the illustrated embodiment, the front edge 24 is substantially straight while the rear edge 28 is rounded so as to form a rear projection 30 that extends rearwardly from the rear arms 18, 20. The body portion 12 further comprises lateral edges 32 and 34. As is apparent from FIG. 1, the lateral edges 32, 34 extend from the front side 22 to the rear side 26 of the body portion 12 (i.e., from the front arms 14, 16 to the rear arms 18, 20) at an angle relative to the central axis 21 such that the body portion 12 widens from front to back. With the above-described configuration, the body portion 12 is shaped and configured to support the bladder with the front edge 24 positioned adjacent the bladder neck and the rear edge 28 positioned relatively deep within the pelvis. In such a position, the rounded rear edge 28 is adapted to accommodate the contours of the pelvis interior. By way of example, the body portion 12 has a length (along the central axis 21) of approximately 70 (millimeters) mm.

The front arms 14, 16 extend laterally from the front side 22 of the body portion 12 substantially perpendicular to the central axis 21. In the illustrated embodiment, the front arms 14, 16 are substantially parallel to each other and comprise front edges 36 and 38 that are contiguous with the front edge 24 of the body portion 12. In addition, the front arms 14, 16 comprise rear edges 40 and 42 that are, in some embodiments, substantially parallel to the front edges 36, 38 and to each other. The rear edges 40, 42 join the body portion 12 at rounded inner corners 44 and 46. As is further depicted in FIG. 1, the front arms 14, 16 terminate in rounded ends 48 and 50. By way of example, the front arms 14, 16 span a length of approximately 350 mm.

With continued reference to FIG. 1, the rear arms 18, 20 also extend laterally from the body portion 12 substantially perpendicular to the central axis 21. In the embodiment of FIG. 1, the rear arms 18, 20 are substantially parallel to the front arms 14, 16 and to each other. The rear arms 18, 20 comprise front edges 52 and 54 and rear edges 56 and 58. In some embodiments, the front edges 52, 54 and the rear edges 56, 58 are substantially parallel. Like the front arms 14, 16, the rear arms 18, 20 terminate in ends 60 and 62. Unlike the ends 48 and 50, however, the ends 60 and 62 of the rear arms 18, 20 are pointed due to the provision of angled edges 64 and 66 that extend from the front edges 52, 54 of the arms 18, 20 to the rear edges 56, 58 of the arms. In the illustrated embodiment, the angled edges 64, 66 are angled outwardly from the front of the arms 18, 20 to the rear. As described below, the pointed ends 60, 62 both facilitate threading of the rear arms 18, 20 through an introducer needle as well as aid the surgeon in distinguishing the rear arms from the front arms 14, 16. By way of example, the rear arms span a distance of approximately 395 mm so as to be slightly longer than the front arms 14, 16.

In some embodiments all or at least a portion of the body portion 12 is formed of a relatively soft material as compared to the relatively coarse material of the arms 14, 16, 18, and 20 such that the portion of the implant 10 that supports the bladder is relatively soft and compliant while the arms are less compliant to ensure secure fixation and avoid implant migration. In the embodiment of FIG. 1, a central portion defined by the area bounded by dashed lines 68 and 70 (which extend from the front side 22 to the rear side 26 of the body portion 12) and having a width of approximately 43 mm comprises the relatively soft material. In addition, substantially the entire body portion 12, on both sides, can be provided with a coating of an absorbable, hydrophilic film of porcine collagen. In the embodiment of FIG. 1, the coating covers the area bounded by the hidden lines 72 and 74 (which extend from the front side 22 to the rear side 26 of the body portion 12).

FIG. 2 shows the anterior implant 10 in a perspective view in free space. The flexibility of the implant 10 is apparent from the illustrated orientation of the implant.

Figure 3:
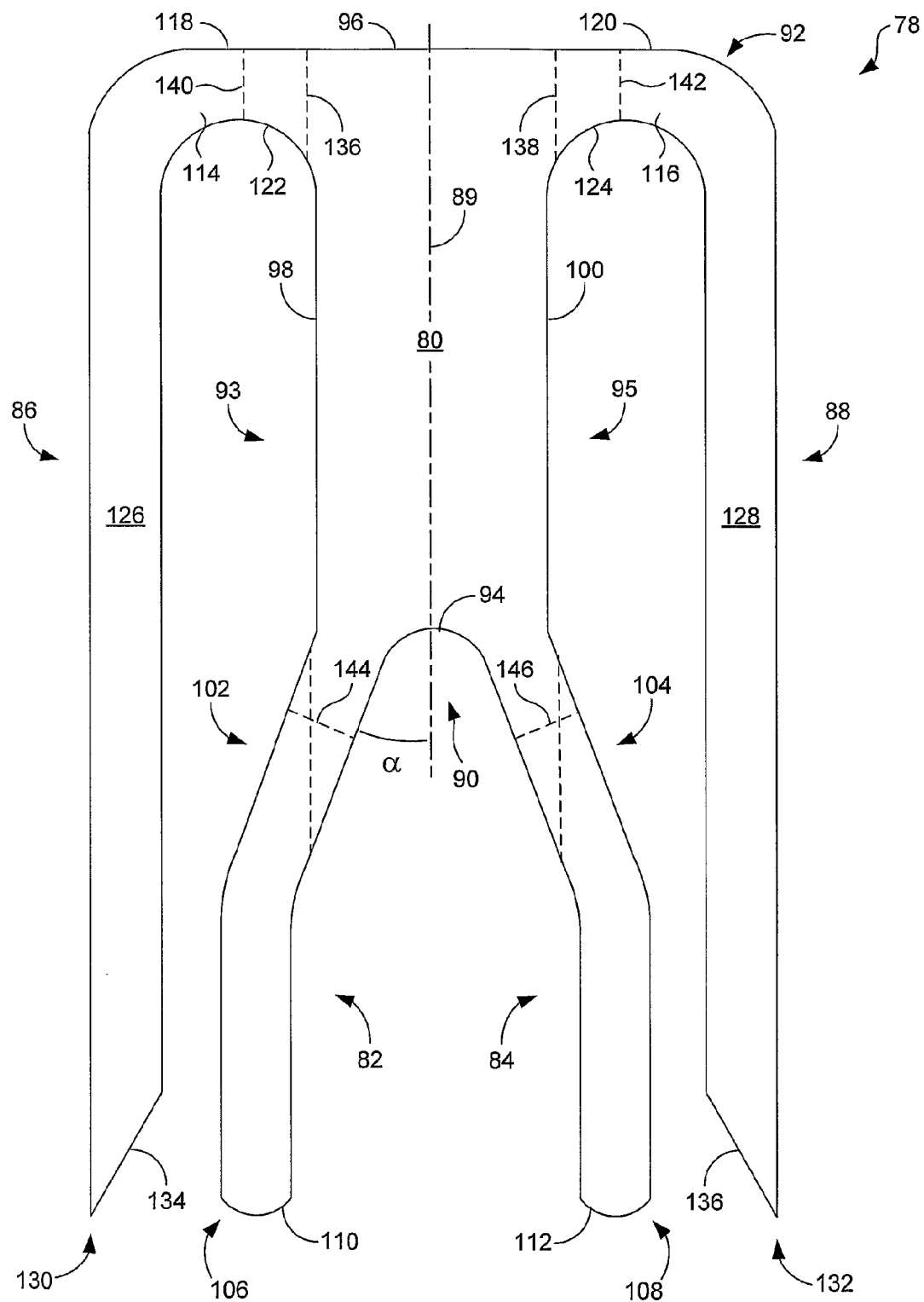
FIG. 3 is a top view of an embodiment of a posterior implant suitable for use in treating rectocele.
Figure 4:
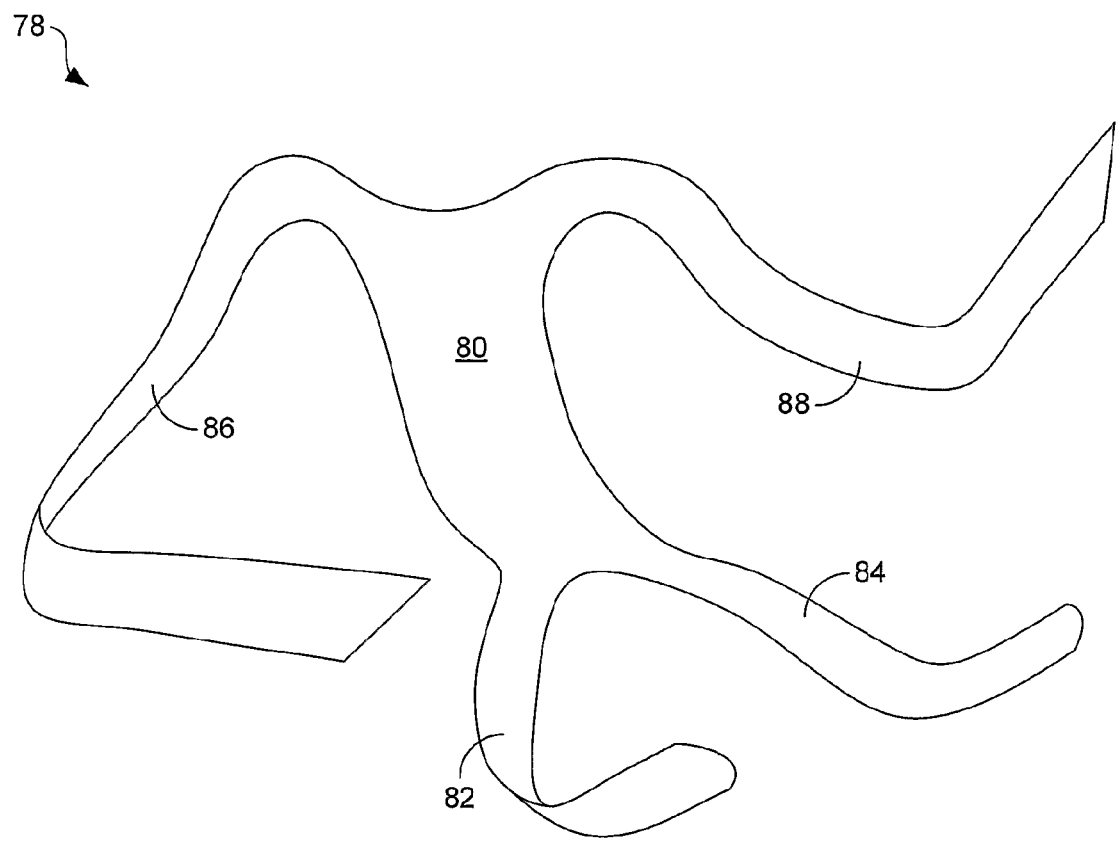
FIG. 4 is a perspective view of the posterior implant of FIG. 3.

FIGS. 3 and 4 illustrate an embodiment of a posterior implant 78, which may be used to treat rectocele. As indicated in FIG. 3, the implant 78 generally comprises an elongated body portion 80, two front arms 82 and 84, and two rear arms 86 and 88. The posterior implant 78 is substantially symmetric about a longitudinal axis 89 that extends along the body portion 80. The body portion 80 is shaped and configured to be positioned between the vagina and the rectum and comprises a substantially rectangular shape defined by front side 90, a rear side 92, and opposed lateral sides 93 and 95. The front side 90 comprises a rounded edge 94 that extends inwardly towards the center of the body portion 80. The rear side 90 comprises a substantially straight edge 96. In addition, the body portion 80 comprises substantially straight lateral edges 98 and 100 that, in some embodiments, are substantially parallel to each other. By way of example, the body portion 80 has a width dimension of approximately 40 mm and length dimension of approximately 100 mm.

The front arms 82, 84 each comprise two sections, first sections 102 and 104 that extend directly from the body portion 80, and second sections 106 and 108 that extend from the first sections 102 and 104. The first sections 102, 104 extend from the body portion 80 at divergent angles relative to the longitudinal axis 89. By way of example, each first section 102, 104 forms an angle, $\alpha$, of approximately 20 degrees with the longitudinal axis 89. The second sections 106, 108 extend from the first sections 102, 104 in a direction that is substantially parallel to the longitudinal axis 89 and to each other. The second sections 106, 108, and the front arms 82, 84 generally, terminate in rounded ends 110 and 112. By way of example, the front arms 106, 108 extend from the body portion 80 a distance of approximately 100 mm.

The rear arms 86, 88 extend from the rear side 92 of the body portion 80 past the front side 90 of the body portion to terminate adjacent the termination point of the front arms 106, 108. In the embodiment of FIG. 3, the rear arms 86, 88 initially extend laterally from the body portion 80 (substantially perpendicular to the longitudinal axis 89) along lateral sections 114 and 116. The lateral sections 114, 116 are defined by substantially straight rear edges 118 and 120, which are contiguous with the rear edge 96 of the body portion, and rounded edges 122 and 124. Extending from the lateral sections 114, 116 are longitudinal sections 126 and 128 that are substantially parallel to the longitudinal axis 89 and to each other. The longitudinal sections 126, 128 terminate in pointed ends 130 and 132 that are defined by angled edges 134 and 136. In the embodiment of FIG. 3, the angled edges 134, 136 diverge outwardly relative to the longitudinal axis 89. As with the pointed ends 60, 62 of the anterior implant 10 (FIG. 1), the pointed ends 130, 132 facilitate threading of the rear arms 86, 88 through a needle and aid the surgeon in distinguishing the rear arms from the front arms 82, 84. By way of example, the rear arms 86, 88 span a distance (from the rear edge 96 of the body portion 80) of approximately 200 mm and are therefore approximately twice as long as the front arms 82, 84.

In some embodiments, all or a portion of the body portion 80 is formed of a relatively soft material as compared to the material of the arms 82, 84, 86, and 88 such that the portion of the implant 78 that is positioned between the vagina and the rectum is relatively soft and compliant while the arms are less compliant to ensure secure fixation and avoid implant migration. In the embodiment of FIG. 3, a central area bounded by dashed lines 136 and 138 (which extend from the rear side 92 past the front side 90 of the body portion 12 and along the front arms 82, 84) and having a width of approximately 43 mm comprises the relatively soft material. In addition, substantially the entire body portion 12, part of the rear arms 86, 88, and part of the front arms 82, 84 are provided with a coating of an absorbable, hydrophilic film of porcine collagen. In the embodiment of FIG. 3, the extent of the coating is identified by the hidden lines 140, 142, 144, and 146, with the lines 140, 142 being substantially parallel to the longitudinal axis 89 and the lines 144, 146 being angled relative to the longitudinal axis.

FIG. 4 shows the posterior implant 78 in a perspective view in free space. The flexibility of the implant 78 is apparent in FIG. 4 from the illustrated orientation of the implant.

Figure 5:
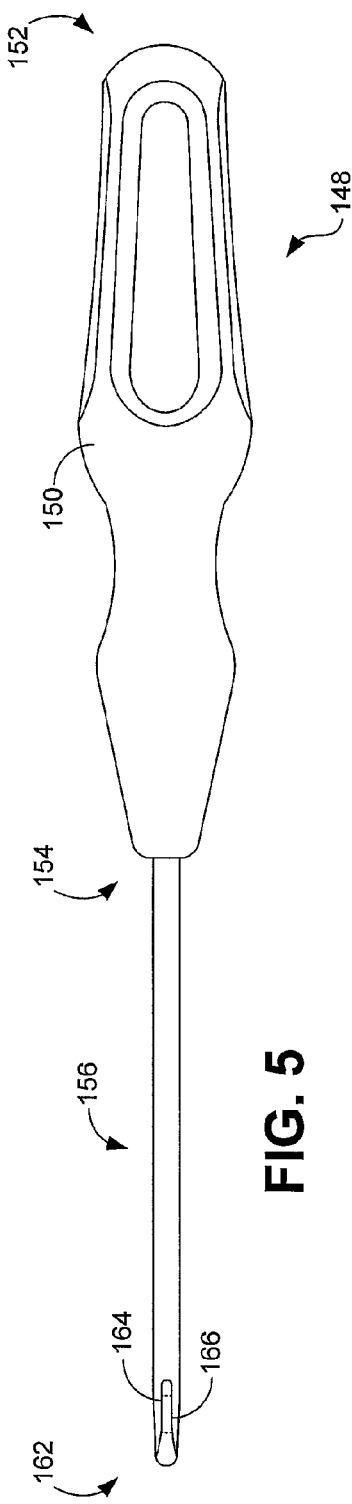
FIG. 5 is a top view of an embodiment of an anterior introducer suitable for use in implanting the anterior implant of FIGS. 1 and 2.
Figure 6:
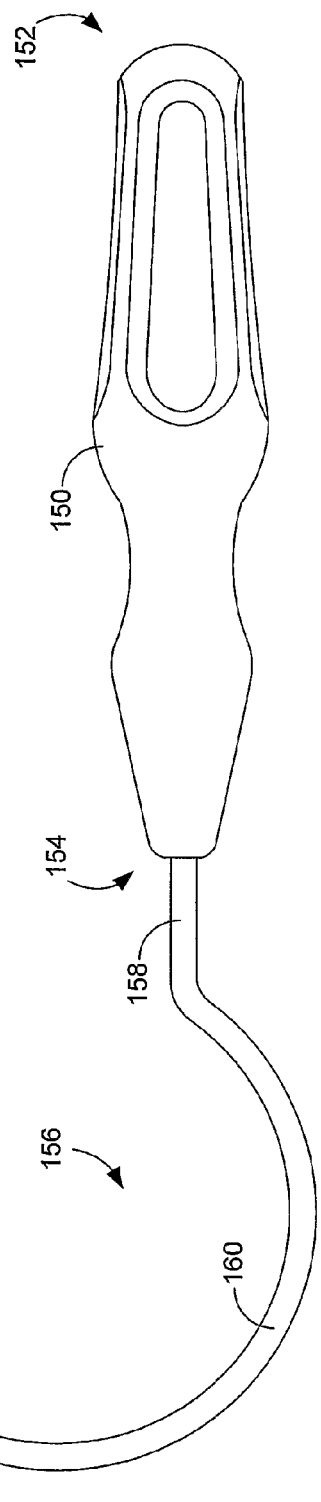
FIG. 6 is a side view of the anterior introducer of FIG. 5.

FIGS. 5 and 6 illustrate an embodiment of an anterior introducer 148, which can be used to implant the anterior implant 10. As indicated in those figures, the introducer 148 comprises a handle 150 that includes a proximal end 152 and a distal end 154. The handle 148 is generally sized and shaped to fit within a surgeon's hand and, as depicted in FIGS. 5 and 6, can be contoured to facilitate firm gripping.

Figure 7:
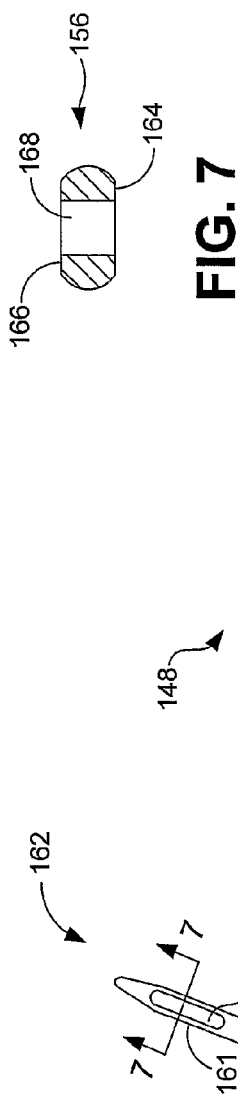
FIG. 7 is a cross-sectional view of a needle of the anterior introducer of FIG. 6 taken along lines 7-7.

A needle 156 extends from the distal end 154 of the handle 150. As shown in FIG. 5, the needle 156 exists substantially within a single plane. As is most clearly shown in FIG. 6, the needle 156 comprises a first substantially straight section 158 that directly extends from the handle 150 substantially parallel to a longitudinal axis of the handle (not identified). Extending from the straight section 158 is a curved section 160. By way of example, the curved section 160 extends along an arc having a radius of curvature of approximately 36.5 mm. The curved section 160 leads to a second substantially straight section 161 that terminates in a blunt tip 162. As is apparent from FIGS. 5 and 7, the straight section 161 is narrowed relative to the remainder of the needle 156 and is defined by two opposed lateral flat surfaces 164 and 166. Returning to FIG. 6, an elongated opening 168 is formed through the straight section 161 adjacent the tip 162. The opening 168 generally extends along the length direction of the needle 156 and serves as an attachment mechanism for releasably attaching an arm of an implant (e.g., anterior implant 10) to the needle. As shown in the cross-sectional view of FIG. 7, the opening 168 extends from one flat surface 164 to the other flat surface 166 of the needle 162. Notably, although an opening has been identified, the needle 156 can be provided with other attachment mechanisms that can secure the implant to the needle.

In terms of materials, the handle 150 can be constructed of any suitable rigid material, such as a metal or a polymeric material. The needle 156 can be constructed of a biocompatible, strong material, such as stainless steel. In some embodiments, the handle 150 and needle 156 can be composed of the same material and may even be unitarily formed together so as to have a monolithic configuration.

Figure 8:
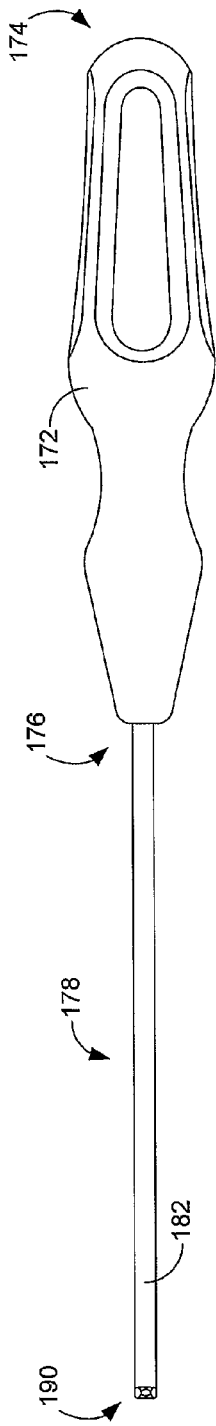
FIG. 8 is a top view of an embodiment of a posterior introducer suitable for use in implanting the posterior implant of FIGS. 3 and 4.
Figure 9:
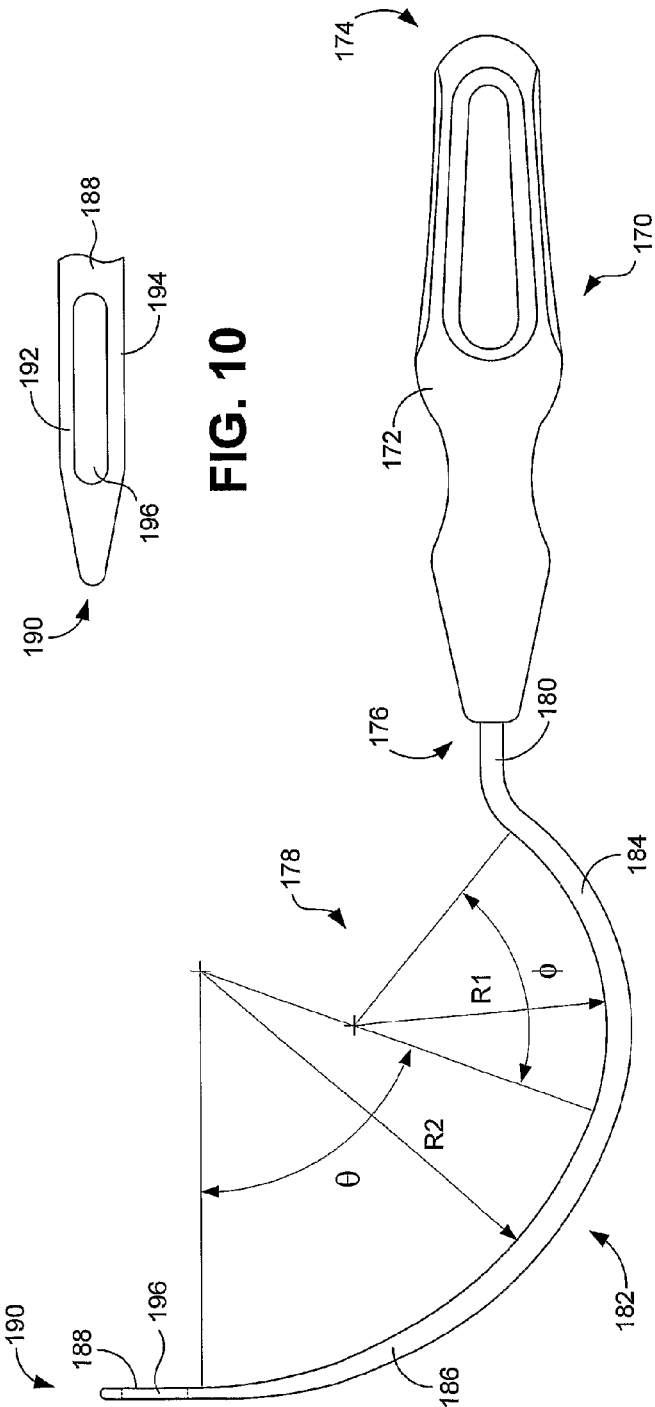
FIG. 9 is a side view of the posterior introducer of FIG. 8.

FIGS. 8 and 9 illustrate an embodiment of a posterior introducer 170, which can be used to implant the posterior implant 78. As indicated in the figures, the introducer 170 comprises a handle 172 that includes a proximal end 174 and a distal end 176. The handle 172 is generally sized and shaped to fit within a surgeon's hand and, as depicted in FIGS. 8 and 9, can be contoured to facilitate firm gripping.

A needle 178 extends from the distal end 176 of the handle 172. As shown in FIG. 8, the needle 178 exists substantially within a single plane. As is most clearly shown in FIG. 9, the needle 178 comprises a first substantially straight section 180 that directly extends from the handle 172 substantially parallel to a longitudinal axis of the handle (not identified). Extending from the straight section 180 is a curved section 182. In the illustrated embodiment, the curved section 182 comprises first curved portion 184 adjacent the straight portion 180 that has a relatively small radius of curvature, and a second curved portion 186 distant from the straight portion that has a relatively large radius of curvature. The two distinct portions 184, 186 of the curved section 182 facilitate manipulation of the needle 178 within the body such that the needle can be passed through an external incision, passed deep into the pelvic cavity adjacent the ischial spine, introduced into the vaginal vault, passed down through the vagina, and exteriorized from the vaginal introitus. More particularly, as is apparent from FIGS. 12A-12E described below, the second curved portion 186 having the greater radius of curvature is used to form a relatively straight passage deep into the pelvic cavity and to traverse the distance from the vaginal vault to the vaginal introitus, while the first curved portion 184 having the smaller radius of curvature is used to rotate or pivot the second curved portion to enable its traversal through the pelvis. By way of example, the first curved portion 184 has a radius of curvature R1 of approximately 48 mm through an angle Φ of approximately 72 degrees, while the second curved portion 186 has a radius of curvature R2 of approximately 78 mm through an angle θ of approximately 70 degrees, such that the second curved portion has a radius of curvature that is nearly twice that of the radius of curvature of the first curved portion.

Figure 10:
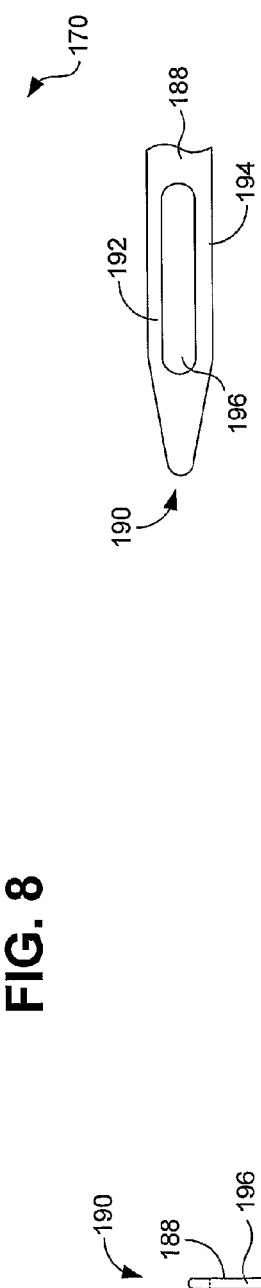
FIG. 10 is a detail view of a portion of the anterior introducer needle of FIGS. 8 and 9.

Extending from the second curved portion 186 is a second substantially straight section 188 that is substantially perpendicular to the first substantially straight section 180 and that terminates in a blunt tip 190. As is most clearly shown in the detail view of FIG. 10, the straight section 188 comprises substantially flat opposed edges 192 and 194. Between those edges is an elongated opening 196 that serves as an attachment mechanism for releasably attaching an arm of an implant (e.g., posterior implant 78) to the needle 178. Notably, while the opening 168 of the anterior introducer 148 may be said to extend laterally through the needle 156, the opening 196 of the posterior introducer 170 extends proximally to distally through the needle 178. Although an opening has been identified, the needle 178 can be provided with other attachment mechanisms that can secure the implant to the needle.

In terms of materials, the handle 172 can be constructed of any suitable rigid material, such as a metal or a polymeric material. The needle 178 can be constructed of a biocompatible, strong material, such as stainless steel. In some embodiments, the handle 172 and needle 178 can be composed of the same material and may even be unitarily formed together so as to have a monolithic configuration.

Figure 11A:
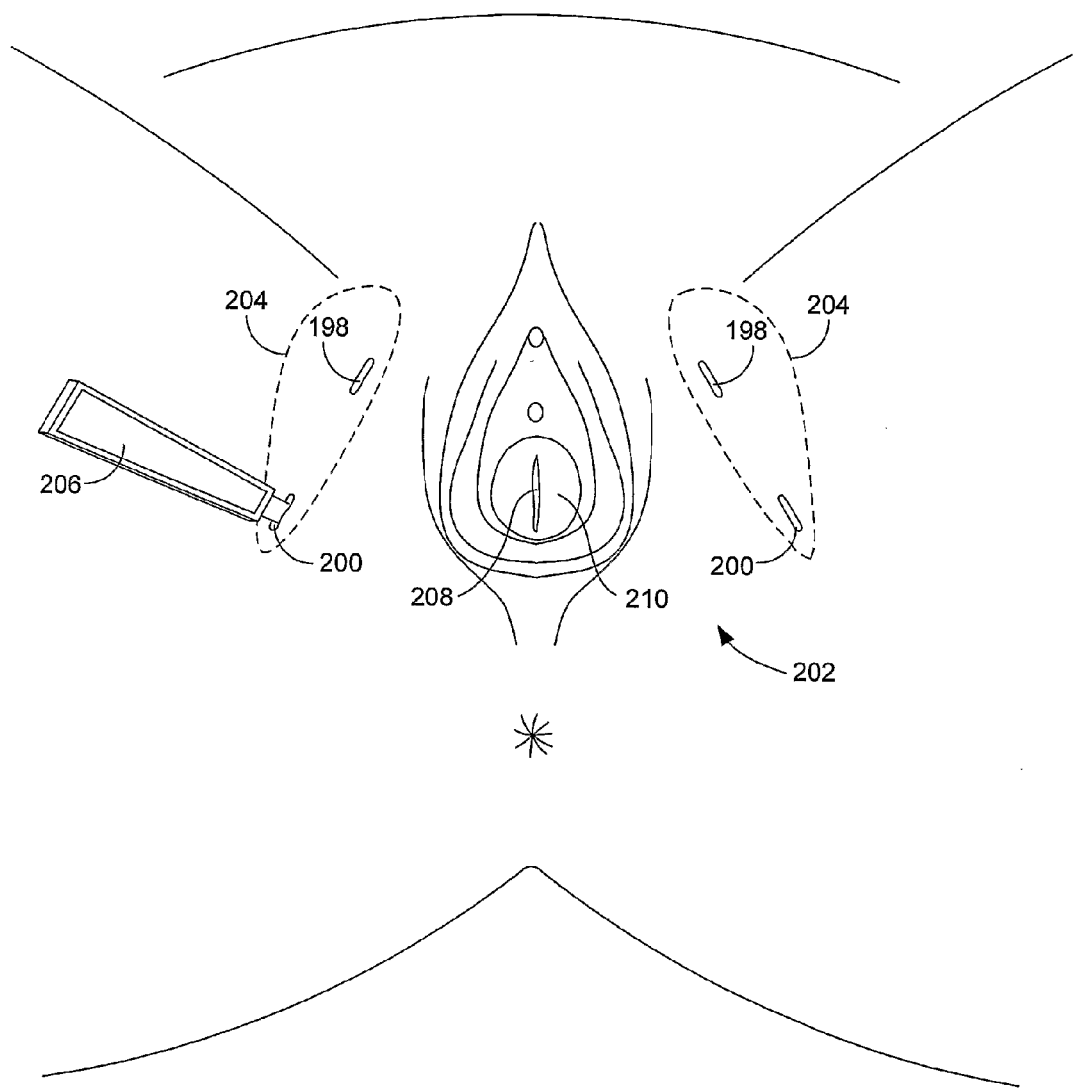
FIGS. 11A-11F illustrate steps performed in an embodiment of a method for implanting the anterior implant of FIGS. 1 and 2.

FIGS. 11A-5F illustrate an embodiment of a method for implanting a pelvic implant. More particularly, FIGS. 11A-11F illustrate a procedure for implanting the anterior implant 10 between the vagina and the bladder using the anterior introducer 148. Beginning with FIG. 11A, superior and inferior incisions 198 and 200 are made in the paravaginal region 202 in alignment with the obturator foramina 204 of the pubic bone (not shown). Those incisions 198, 200 can be made with a sharp device, such as a scalpel 206. In addition, a midline incision 208 can be made in the anterior vaginal wall 210 to provide access to the space between the vagina and the bladder. That space can then be separated by blunt and/or sharp dissection.

Figure 11B:
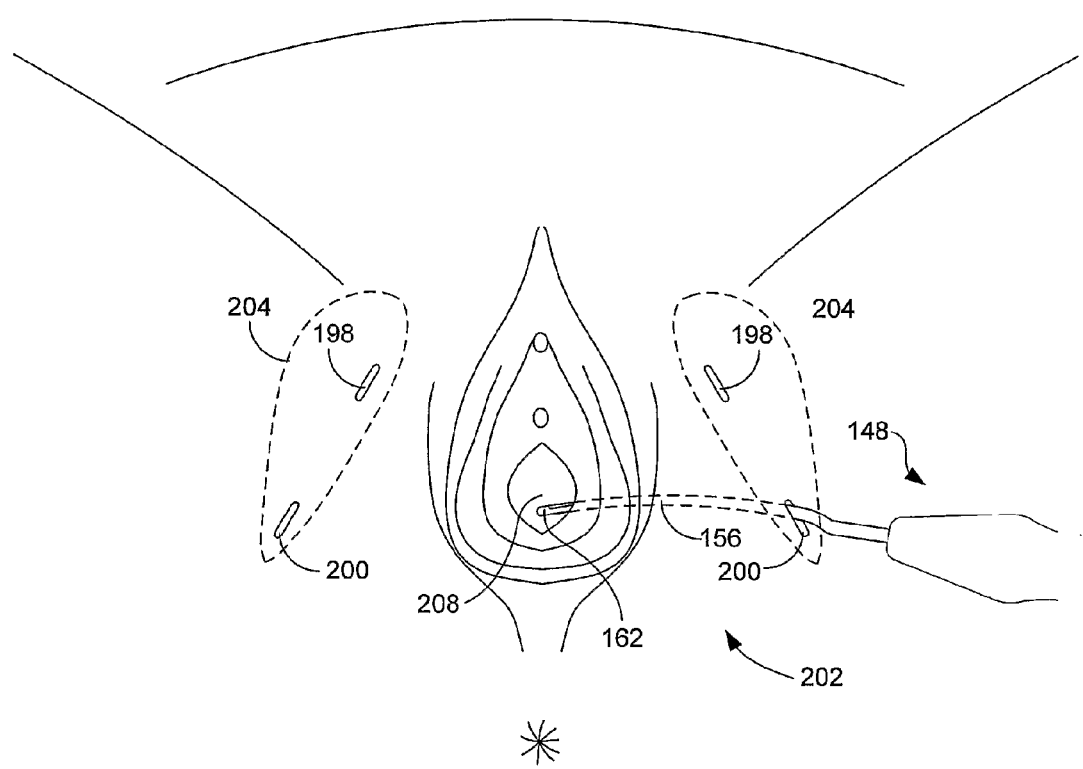
Figure 11C:
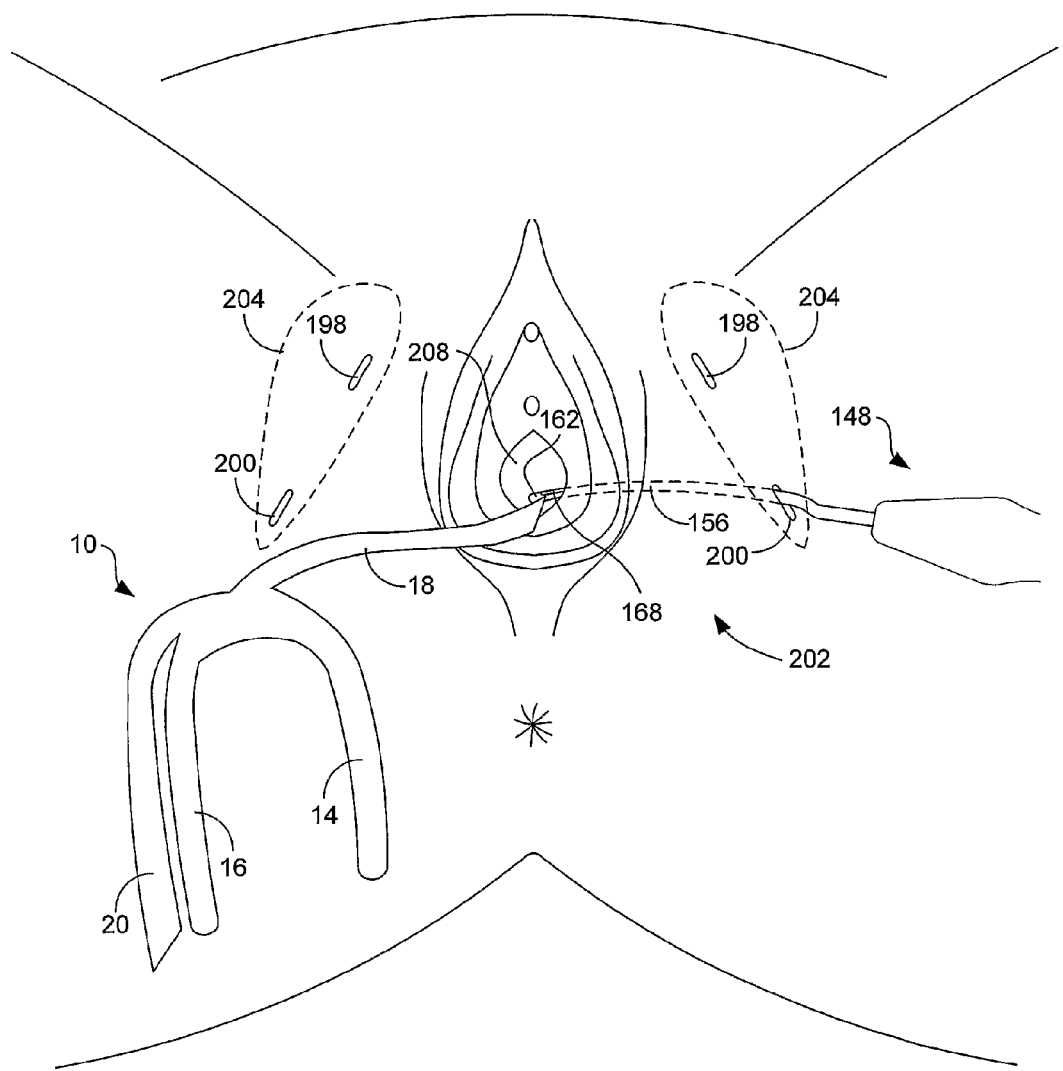

Turning to FIG. 11B, the needle 156 of the anterior introducer 148 is passed through one of the inferior incisions 200 and through the soft tissue of the pelvis until the tip 162 emerges from the vaginal incision 208 to become visible to the surgeon. Referring to FIG. 11C, the anterior implant 10 can then be associated with the needle 156. More particularly, one of the arms of the implant (e.g., rear arm 18) is passed through the opening 168 formed in the needle 156 adjacent the needle tip 162. Notably, the surgeon can easily distinguish between the rear arms and the front arms of the implant 10 due to the pointed tips of the rear arms.

Figure 11D:
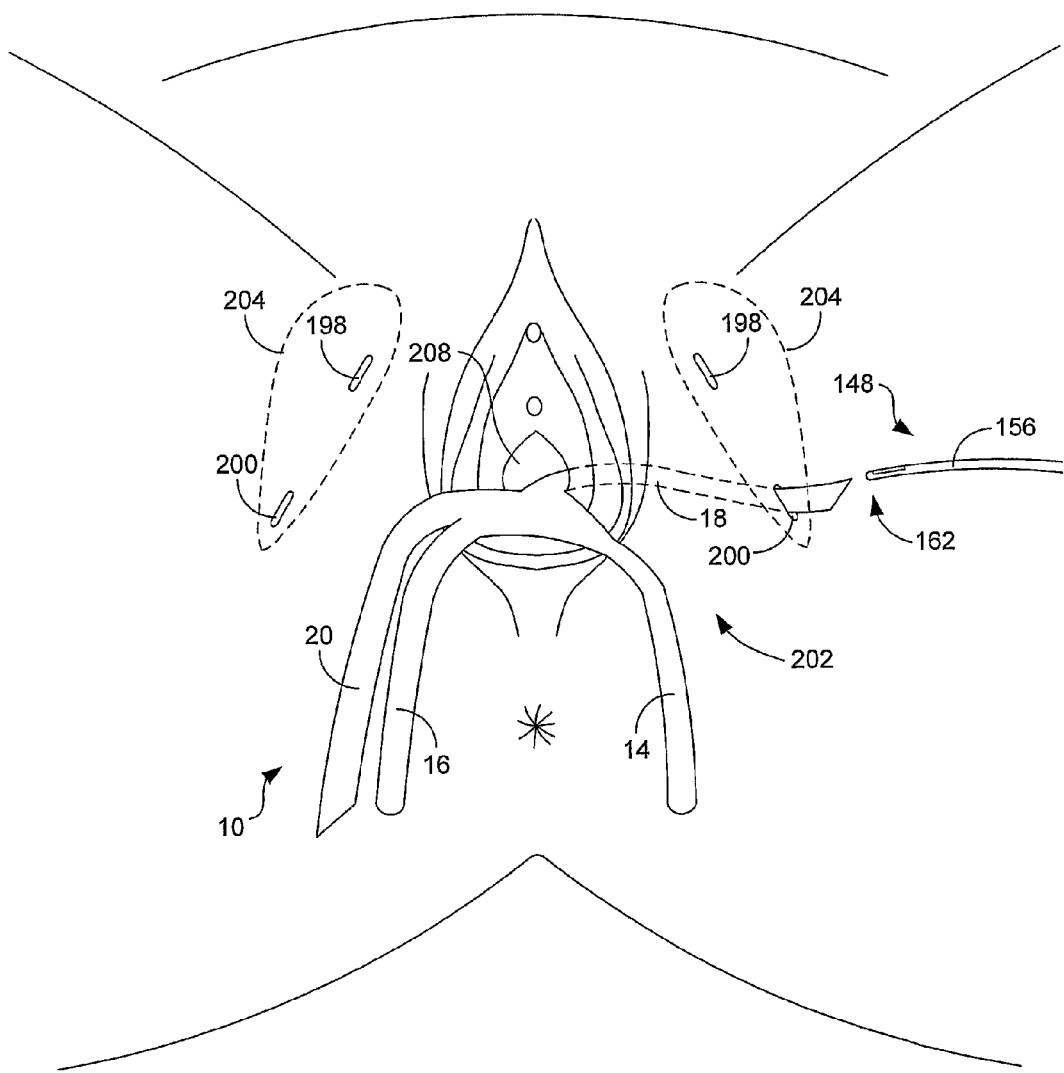

Once the implant arm 18 is associated with the needle 156, the needle may be drawn back through the passage it formed pulling in the implant arm in tow until the needle exits the body and the implant arm occupies the passage and extends out from the inferior incision 200, as indicated in FIG. 11D.

Figure 11E:
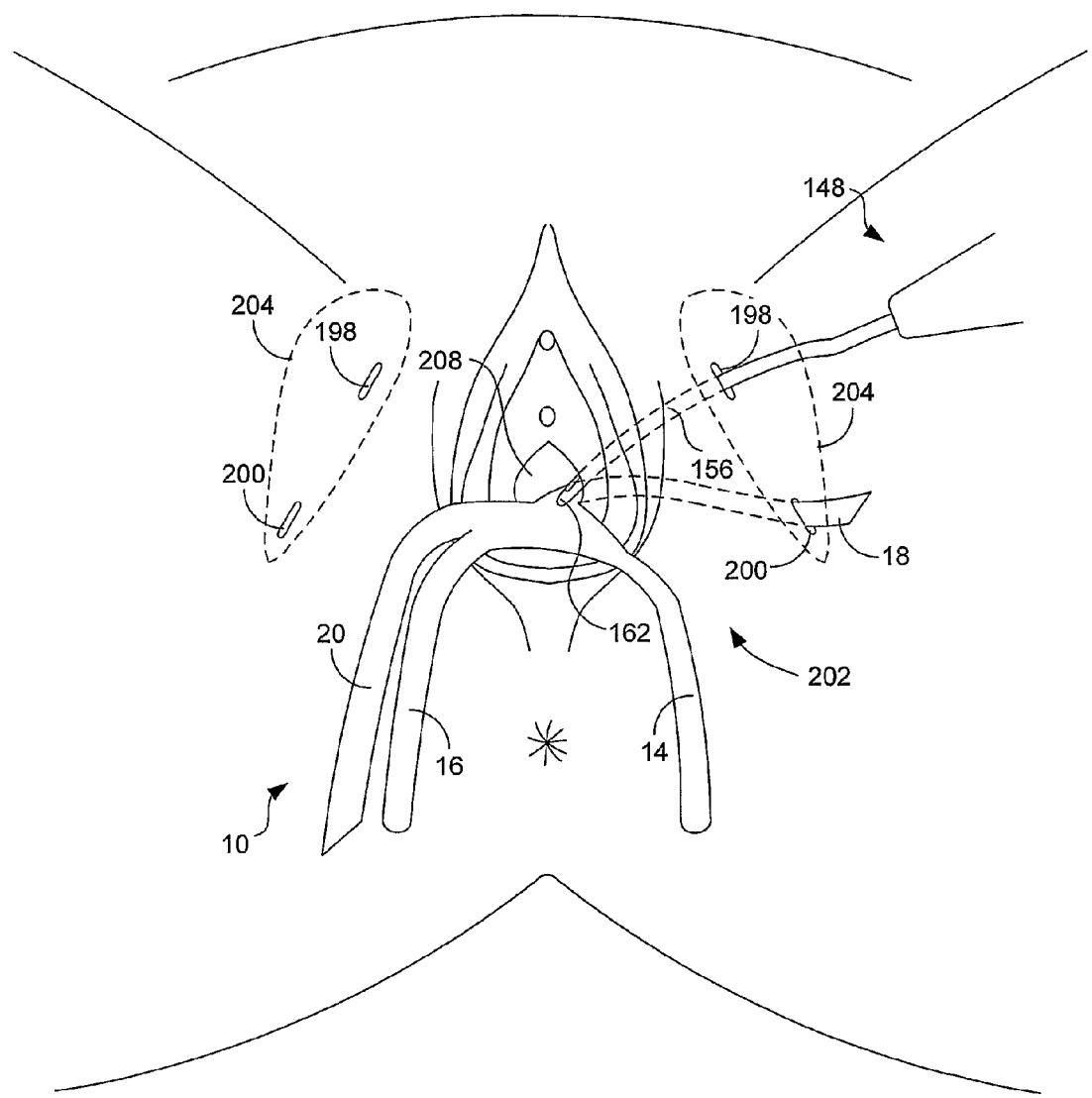

At that point, one of the front arms (e.g., arm 14) can be implanted. This is accomplished by passing the needle 156 through one the superior incisions 198, for example the incision adjacent the inferior incision 200 through which the rear arm 18 was passed, until the needle tip 162 emerges from the vaginal incision 208, as indicated in FIG. 11E. The arm 14 can be associated with the needle 156 in similar manner to that described above by passing the arm through the needle opening 168. The arm 14 can then be drawn through the passage formed by the needle 156 in similar manner to that used to draw the rear arm 18 through its passage (not shown).

Figure 11F:
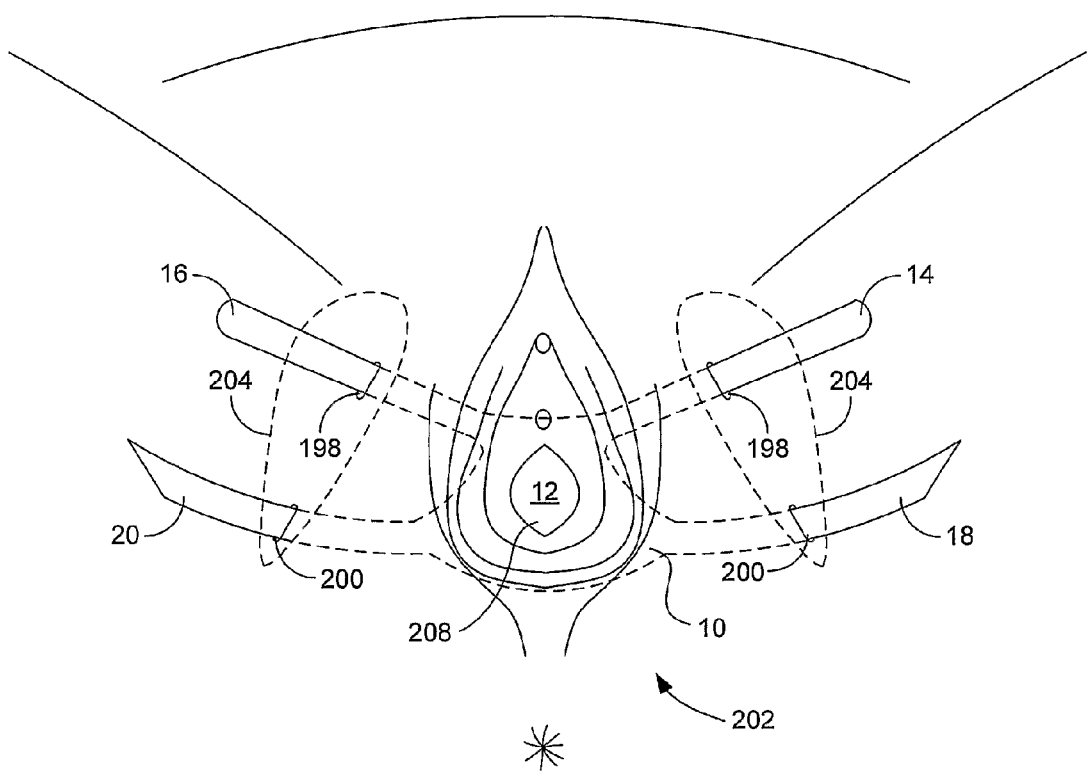

The front and rear arms (e.g., arms 16 and 20) on the opposite side of the implant 10 can then be positioned in similar manner to the methods described above. One or more of the arms can then be tensioned as required to pull the body portion 12 into position between the vagina and the bladder, as indicated in FIG. 11F. At that point, the portions of the arms that extend beyond their respective incisions can be trimmed, the vaginal incision 208 can be closed, and the various external incisions can be closed.

FIGS. 12A-12L illustrate a further embodiment of a method for implanting a pelvic implant. More particularly, FIGS. 12A-12L illustrate a procedure for implanting the posterior implant 78 between the vagina and the rectum using the posterior introducer 170. Beginning with FIG. 12A, small pararectal incisions 210 are made on either side of the anus 212 with a sharp device, such as a scalpel 214. By way of example, the incisions 210 are made 2-3 centimeters (cm) posterior and lateral to the anus 212. In addition, a midline incision is made in the posterior vaginal wall 216 to form an opening 218 that extends from the vaginal introitus to the vaginal apex to provide access to the space between the vagina and the rectum. The vaginal mucosa may then be dissected away from the rectum using blunt and/or sharp dissection.

Figure 12A:
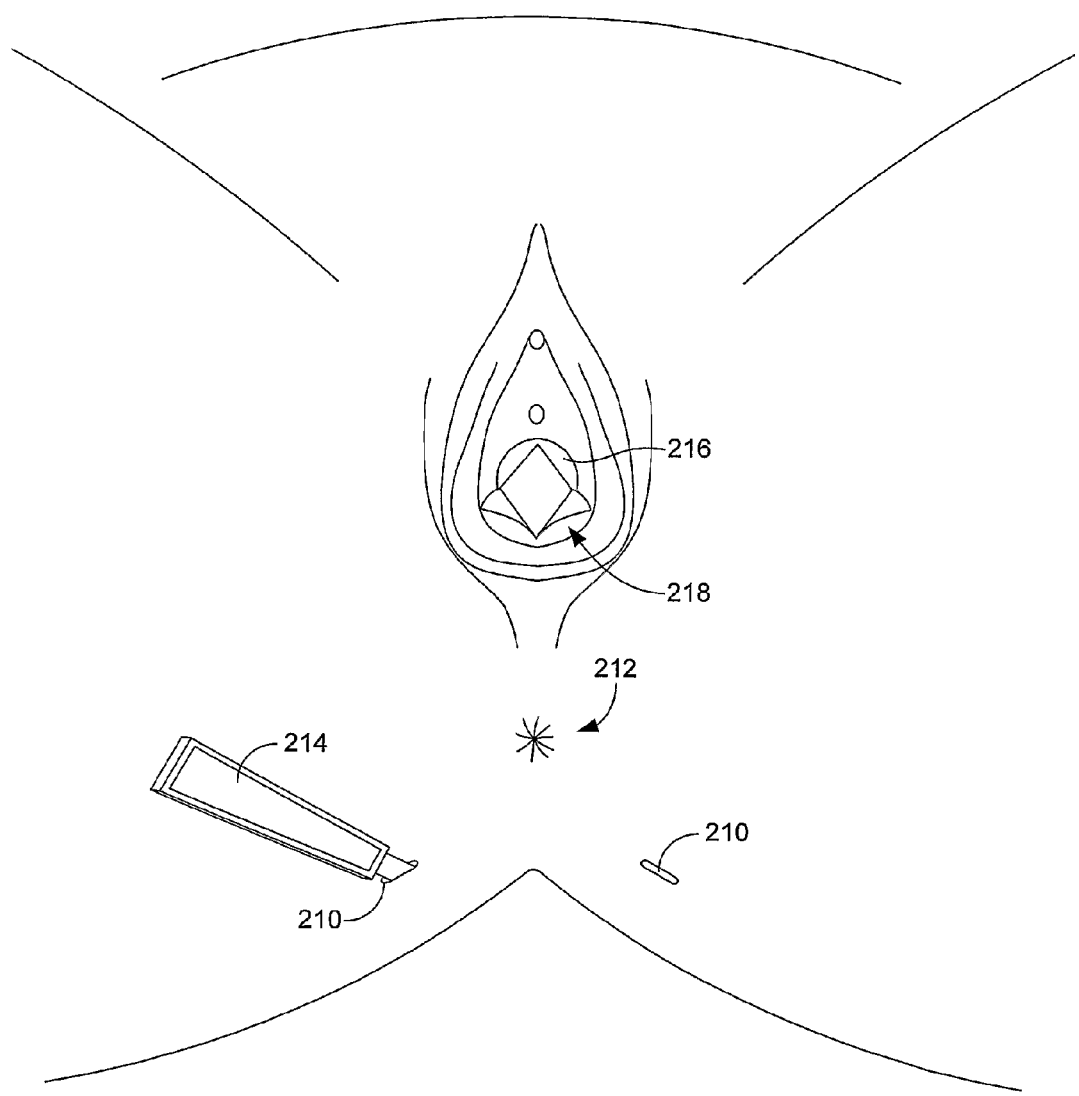
FIGS. 12A-12L illustrate steps performed in an embodiment of a method for implanting the posterior implant of FIGS. 3 and 4.
Figure 12B:
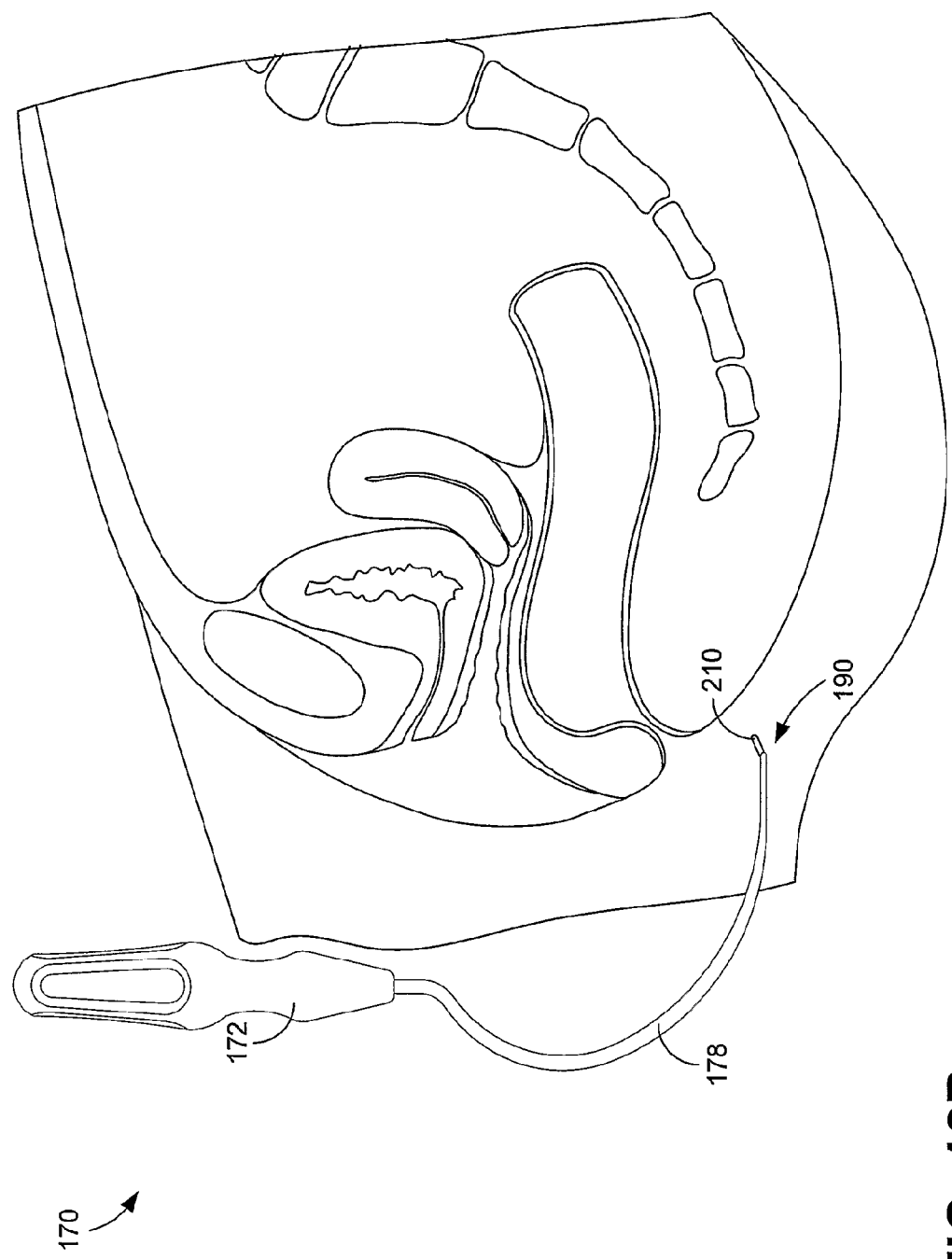
Figure 12C:
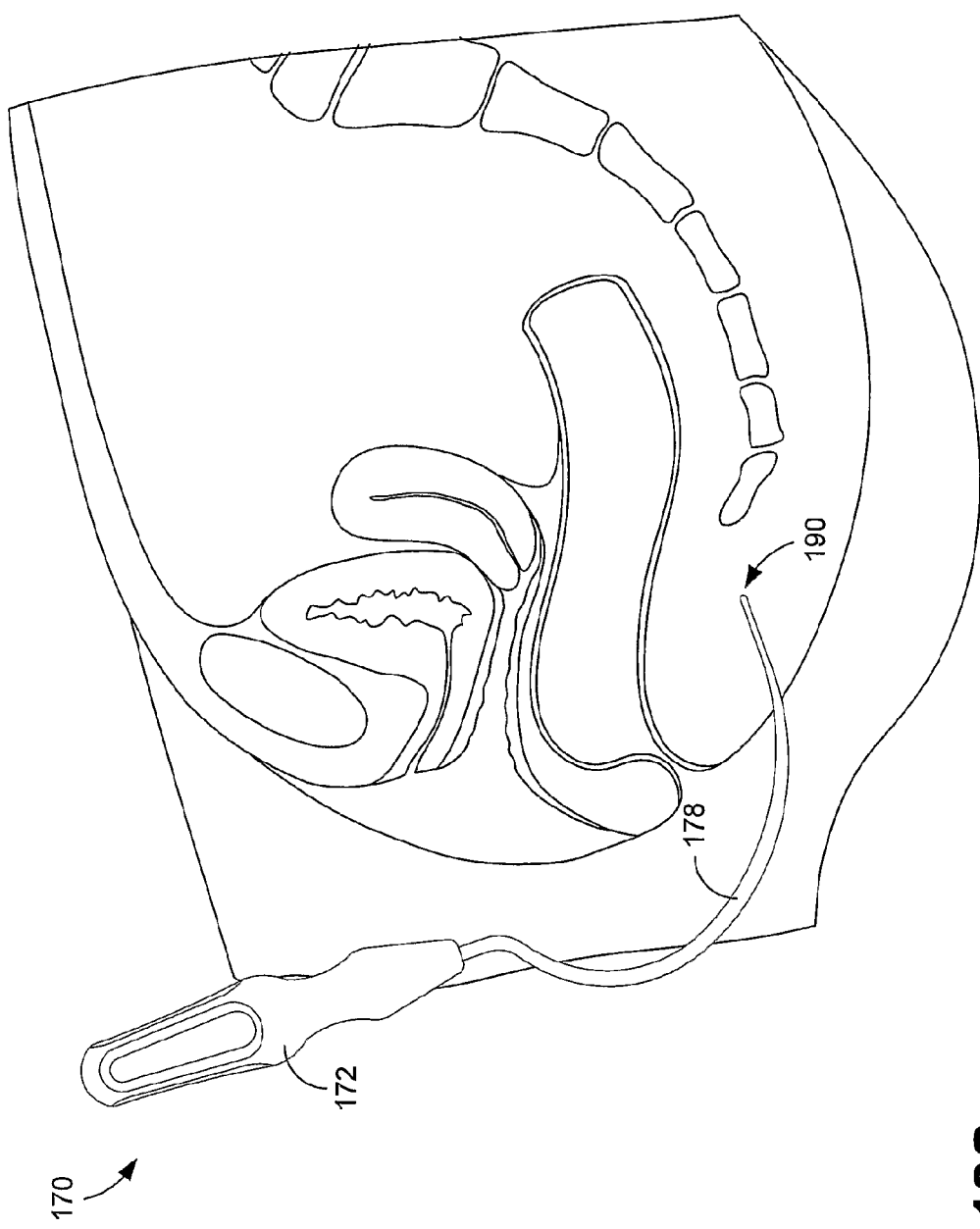
Figure 12D:
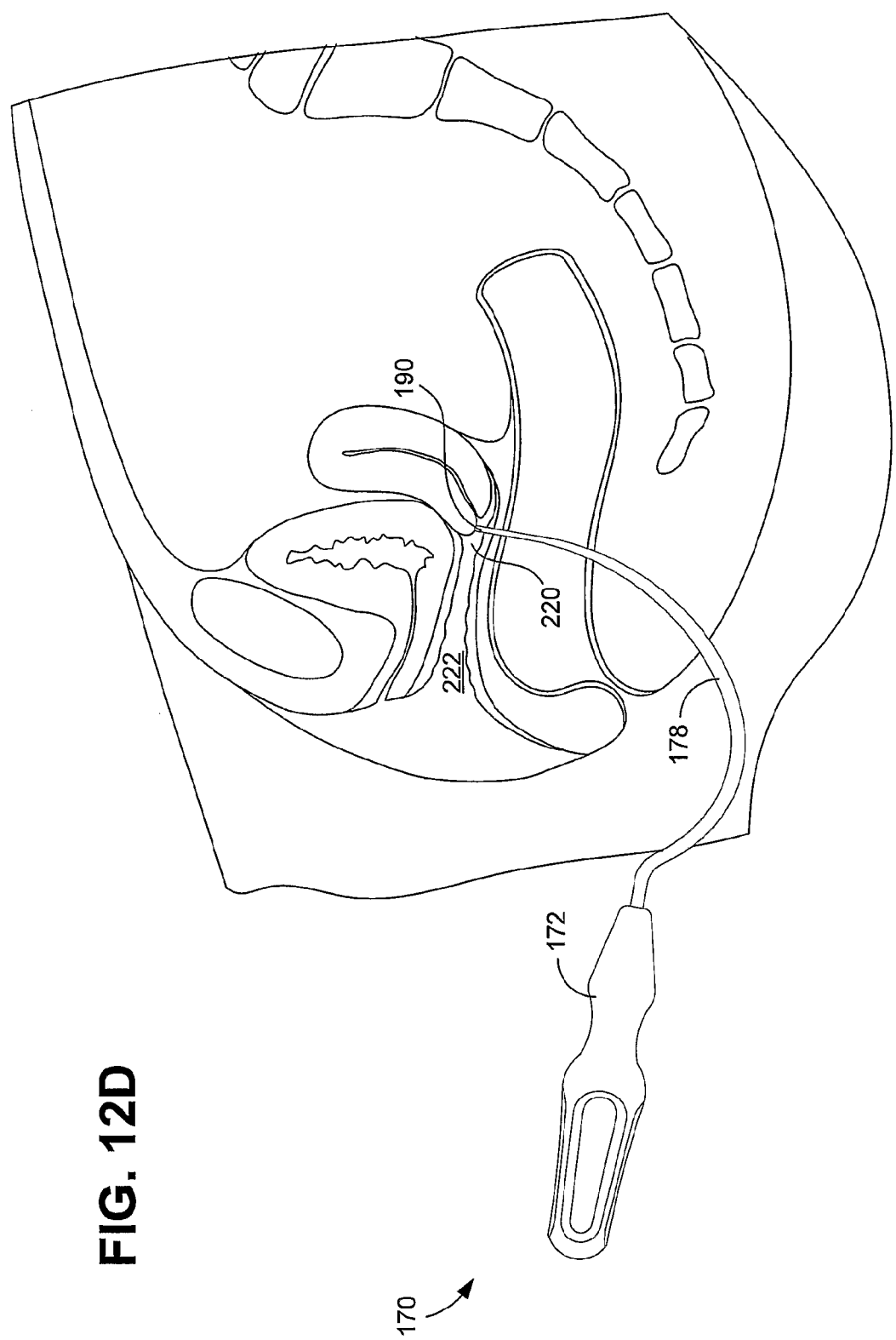

Turning to FIG. 12B, the tip 190 of the posterior introducer needle 178 is positioned at one of the incisions 210 with the introducer 170 oriented so that the handle 172 is generally vertical. Referring next to FIG. 12C, the introducer needle 178 is passed through the incision 210 and through the soft tissue of the pelvis toward the ischial spine (not identified). As the needle 178 passes through the soft tissue, the introducer 170 is rotated so that the handle 172 approximates a generally horizontal orientation, as indicated in FIG. 12D. As is further shown in FIG. 12D, the needle tip 190 is advanced through the posterior vaginal wall and into the vaginal vault 220 such that the tip is positioned within the vagina 222. That process can be aided by placing a finger (not shown) within the vagina 222 to guide the needle tip 190 into position.

Figure 12E:
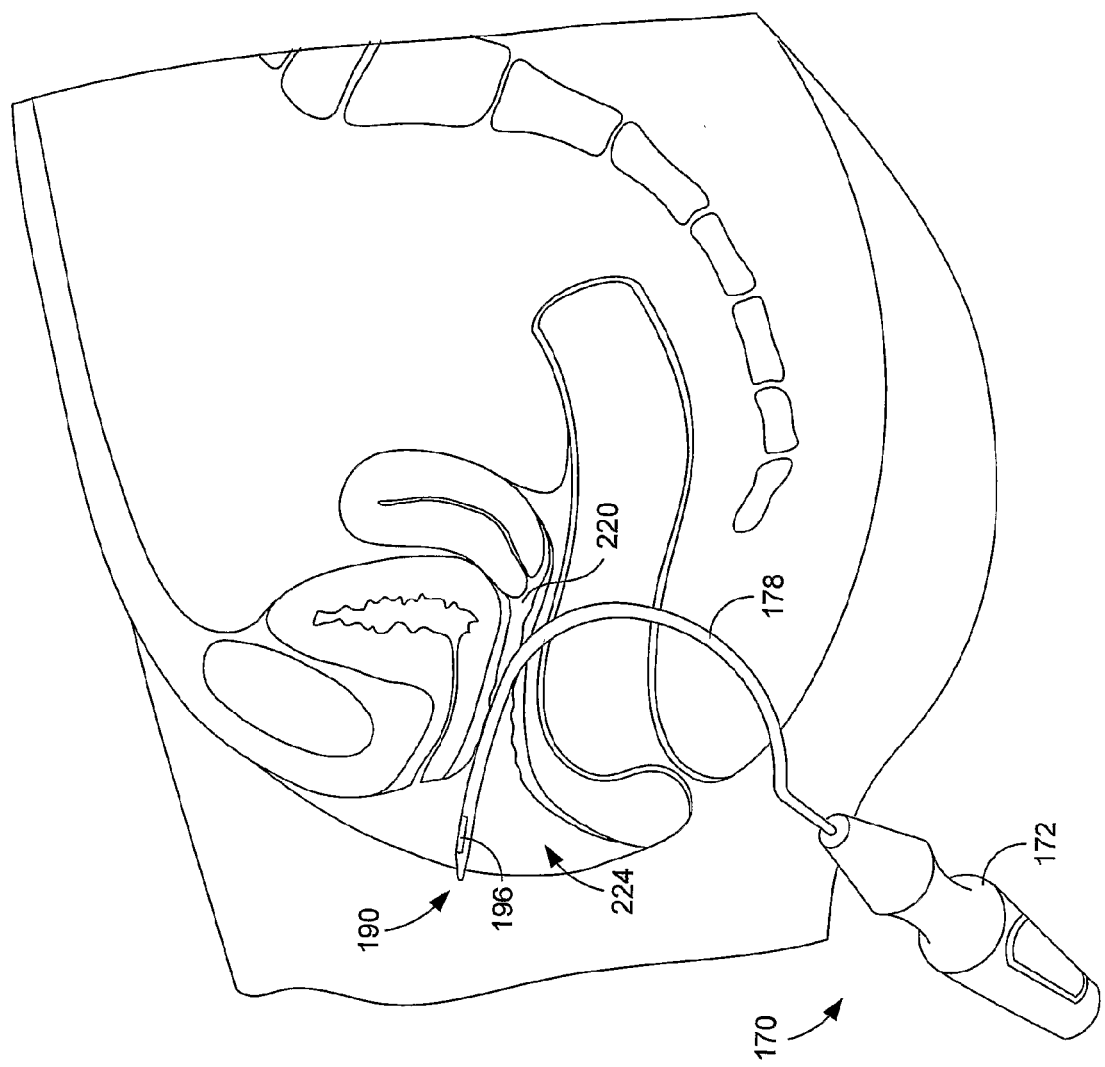

With reference next to FIG. 12E, the introducer handle 172 is pivoted downwardly and rotated laterally relative to the patient to bring the tip 190 of the needle 178 to the vaginal introitus 224 such that the needle tip and the opening 196 adjacent the tip are visible and accessible to the surgeon.

Figure 12F:
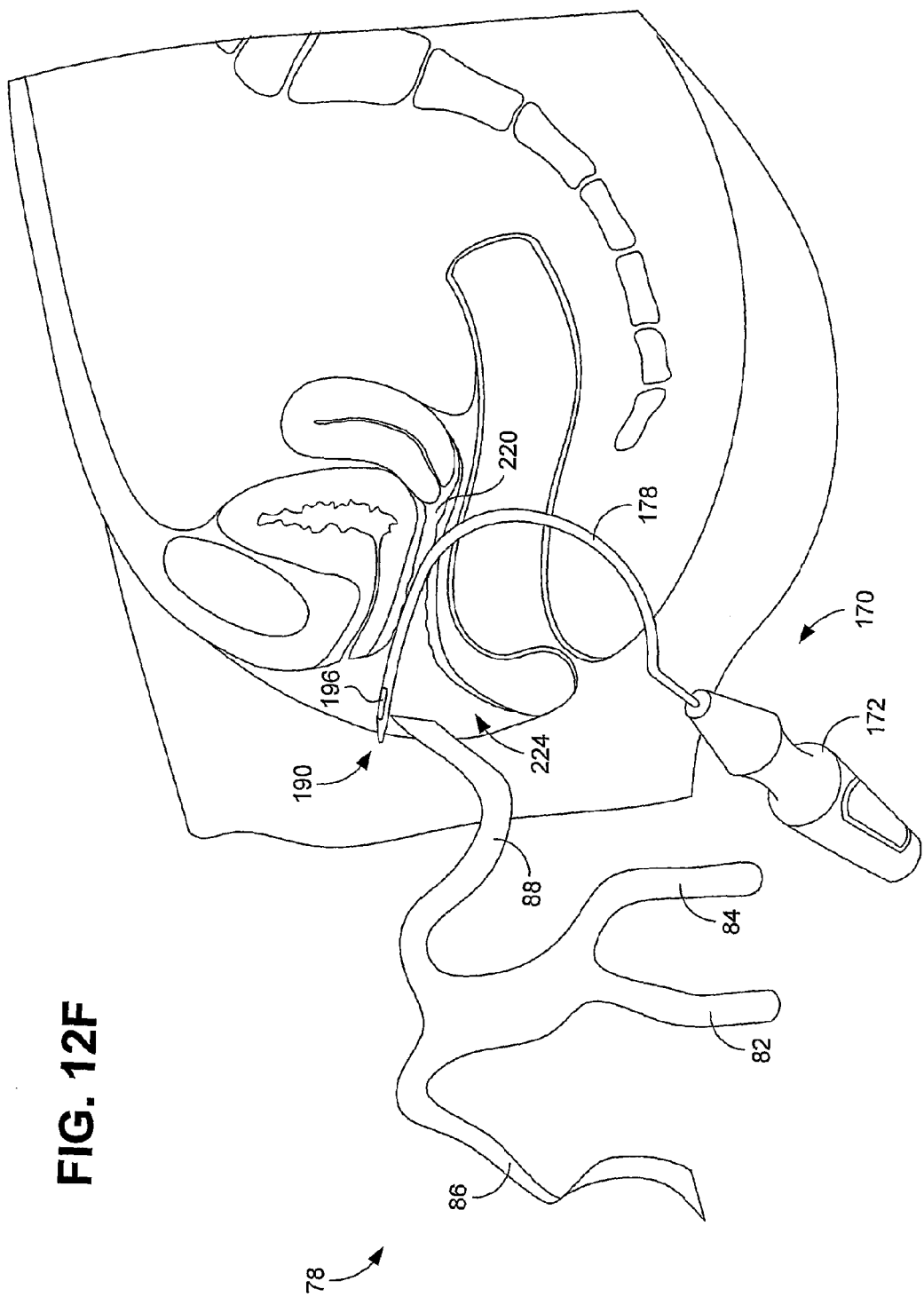

Referring next to FIG. 12F, one of the longitudinal arms (e.g., arm 88) of the posterior implant 78 is associated with the needle 178. In particular, the arm 88 is passed through the opening 196 of the needle 178. Again, the surgeon can distinguish the rear arms from the front arms due to the pointed tips of the rear arms.

Figure 12G:
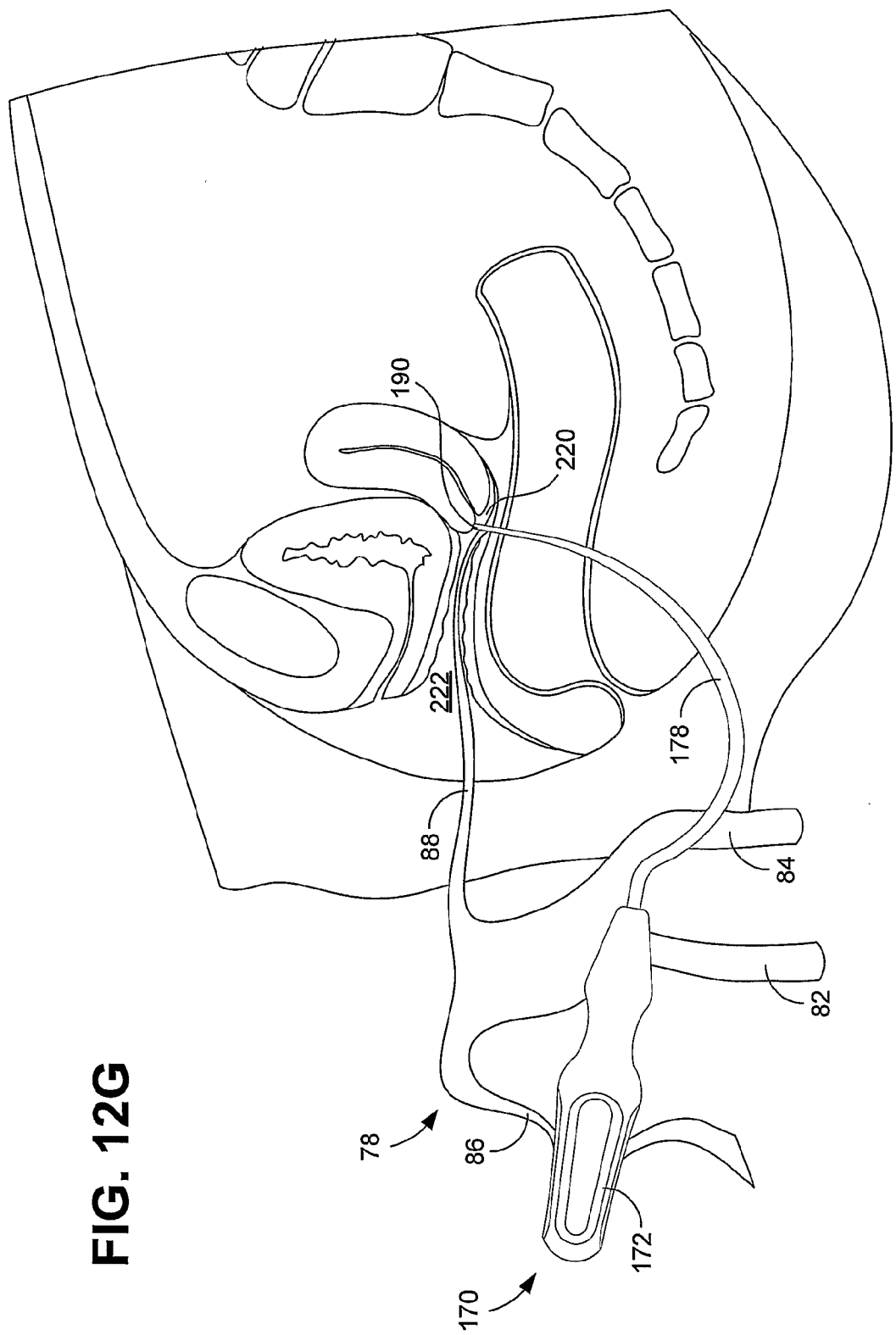
Figure 12H:
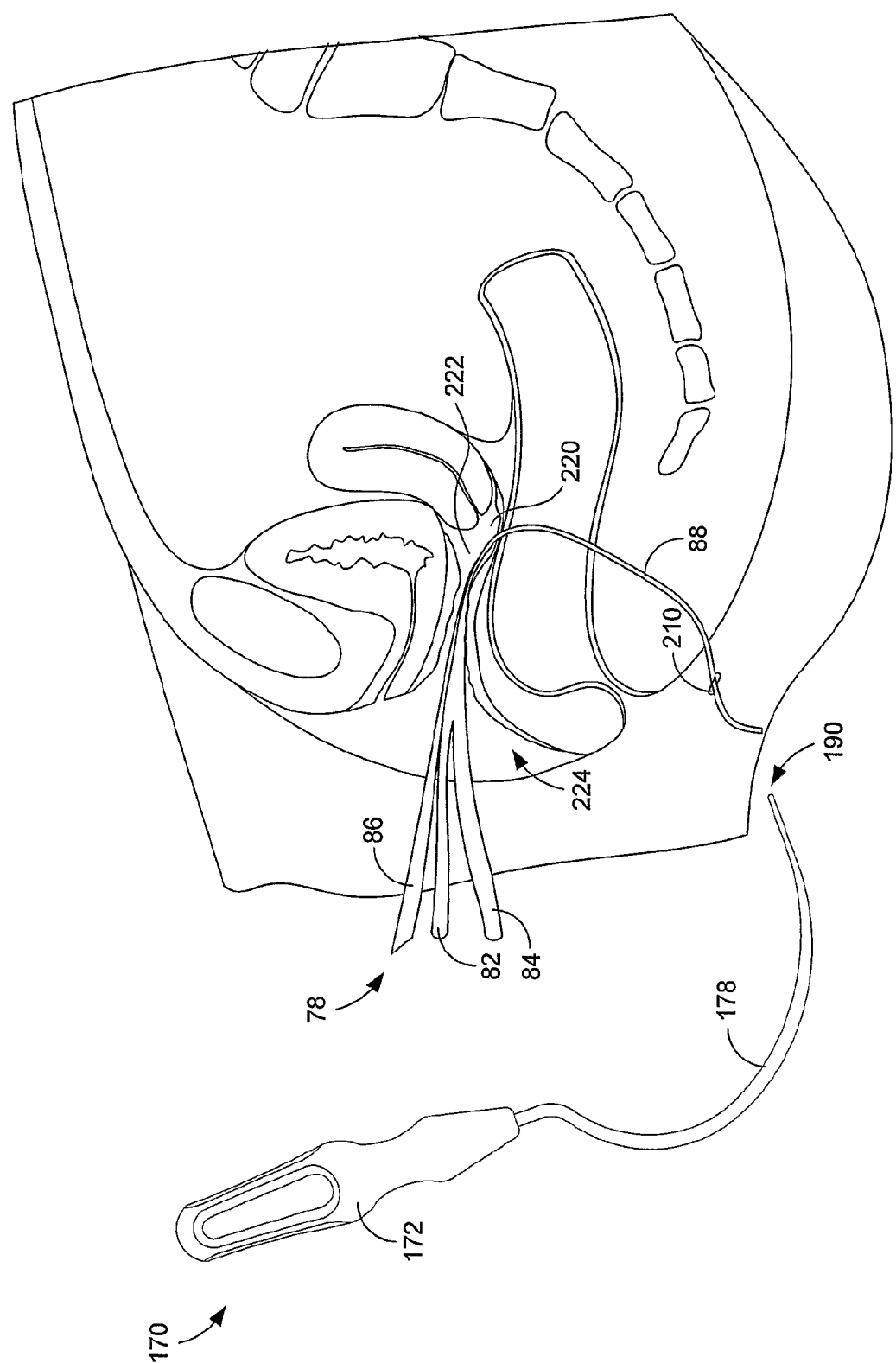

Turning to FIG. 12G, the needle tip 190 can be retracted along the vagina 222 to the vaginal vault 220 to draw the implant arm 88 back toward the vaginal vault. Referring to FIG. 12H, the implant arm 88 can further be drawn through the passage formed by the needle 178 until the arm extends through the pelvis and out through the pararectal incision 210. At that point, the implant arm 88 can be disassociated from the needle 178.

Figure 12I:
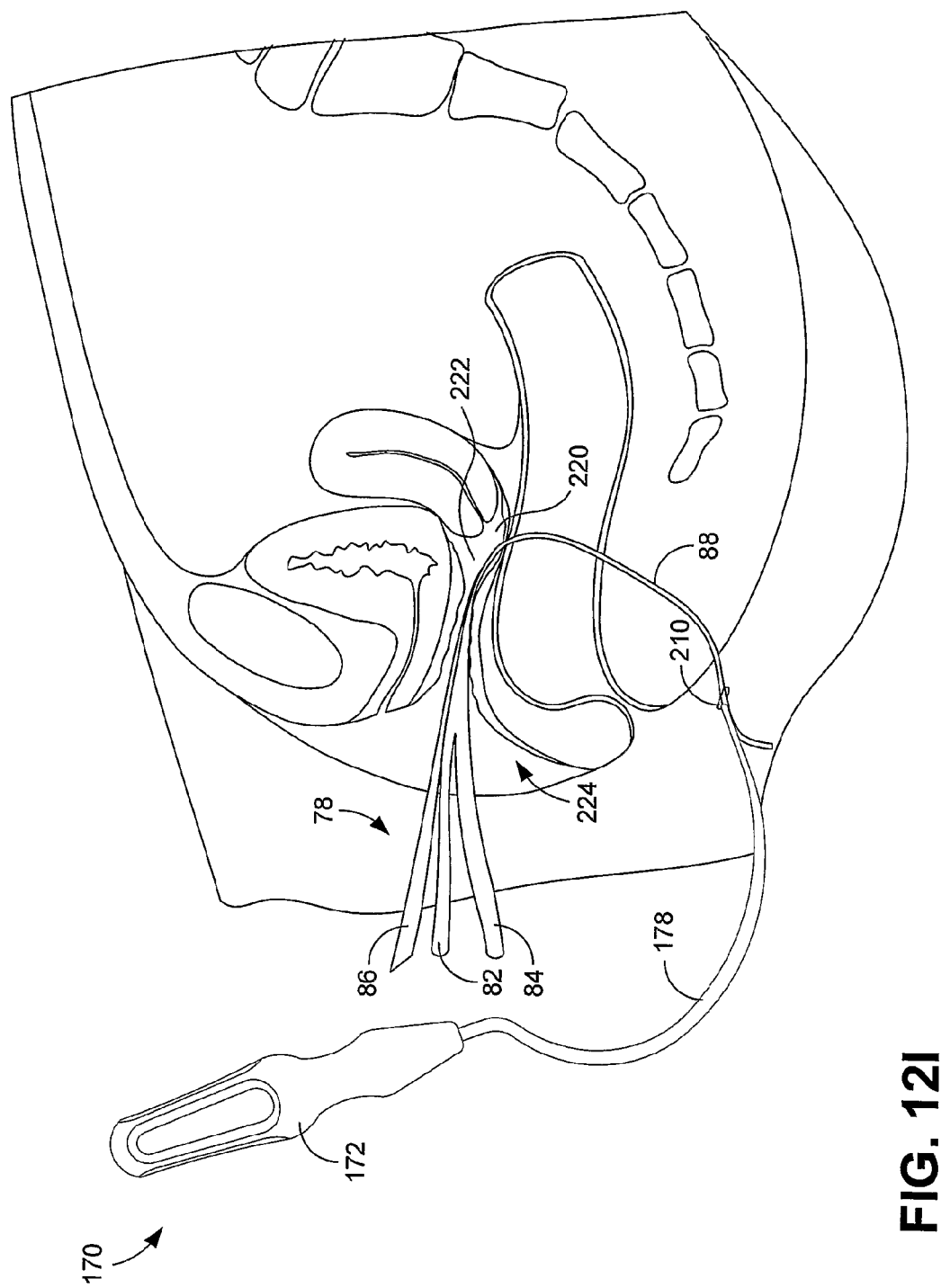
Figure 12J:
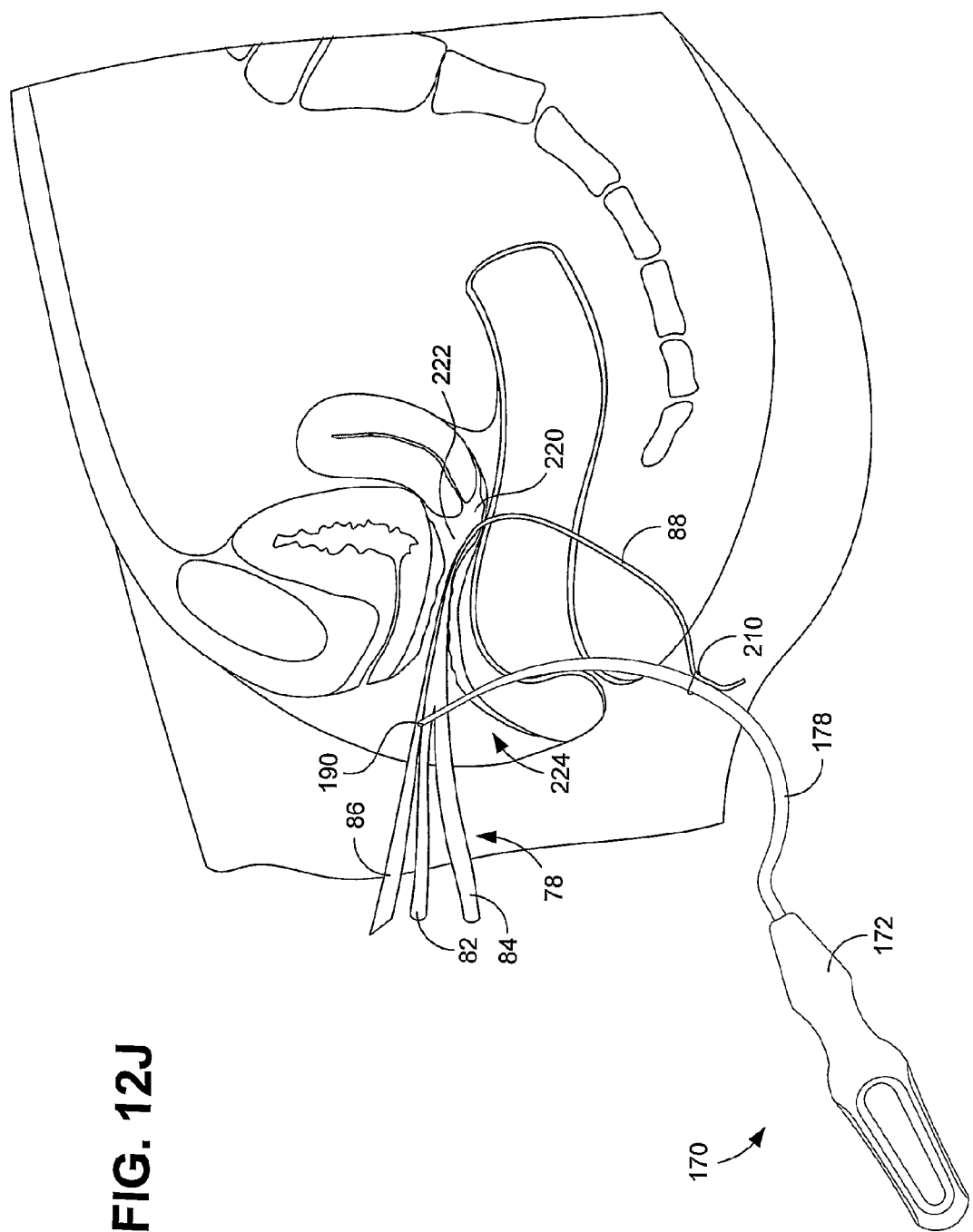

Next, as indicated in FIG. 12I, the needle 178 can be reintroduced through the same pararectal incision 210 from which the implant arm 88 extends in order to position the front arm (e.g., arm 84) on the same side of the implant 78 as the implanted rear arm. As indicated in FIG. 12J, the needle tip 190 is passed along a relatively shallow path through the soft tissue of the pelvis until it emerges from the vaginal introitus 224. At that point, the front arm 84 can be associated with the needle 178 by passing the arm through the opening 196 of the needle, and the arm can be drawn through the pelvis and out through the incision 210 in similar manner to the rear arm 88. Similar procedures may then be performed to implant the anus (e.g., arms 82, 86) on the opposite side of the implant 78 on the opposite side of the vagina.

Figure 12K:
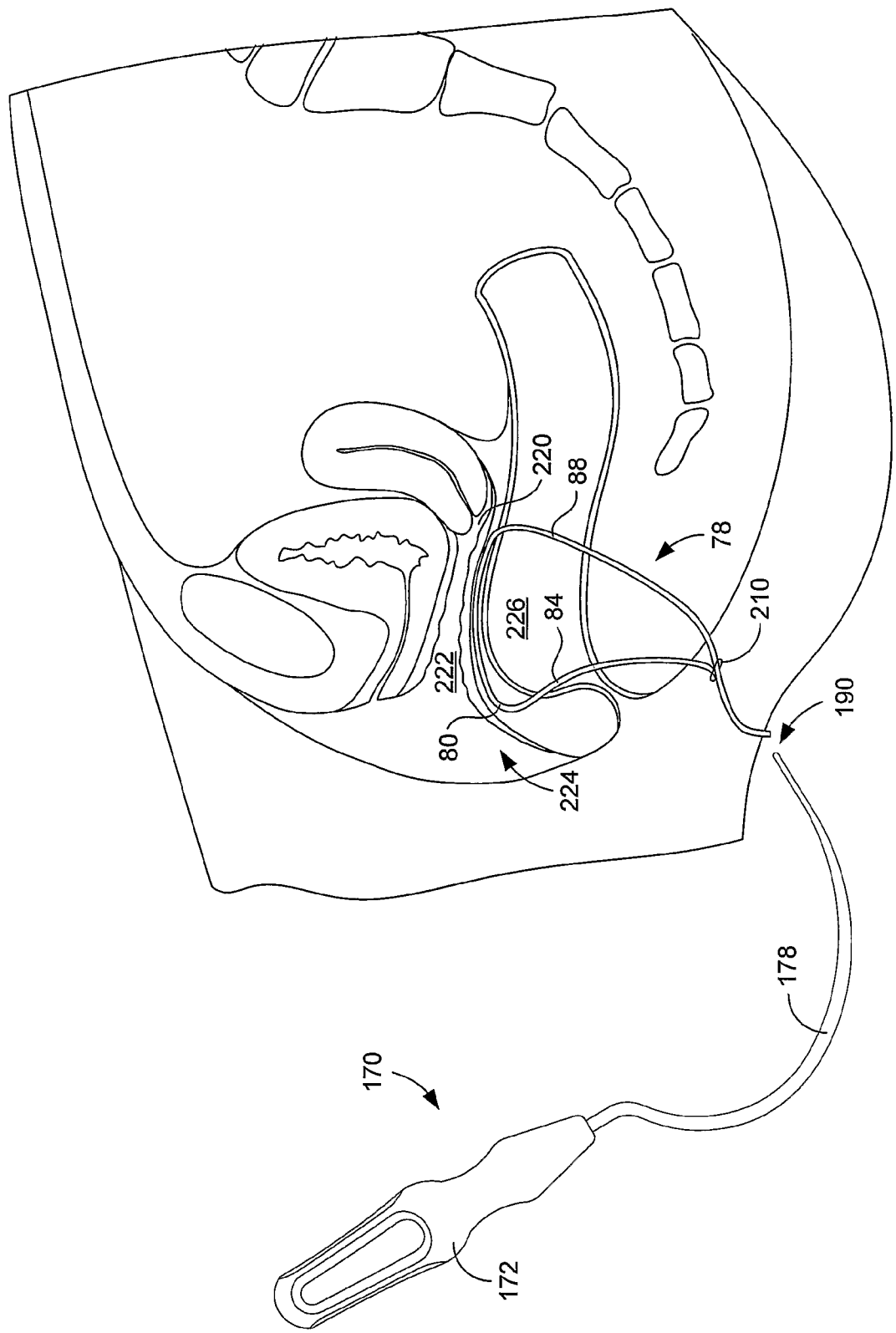
Figure 12L:
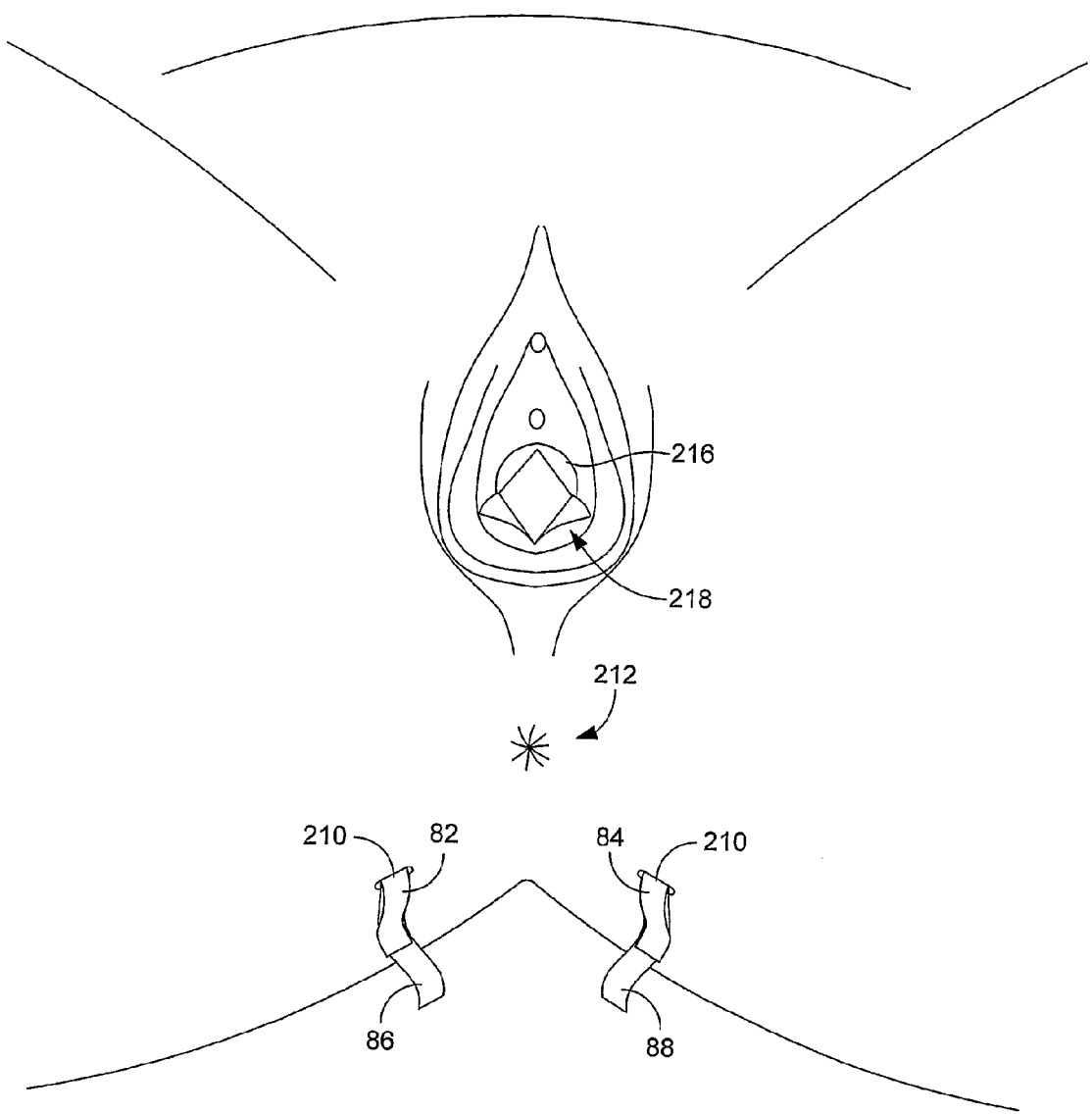

FIG. 12K illustrates the result after each arm has been implanted. As can be appreciated from that figure, the rear arms (only arm 88 visible) are positioned relatively deeply and the front arms (only arm 84 visible) are positioned relatively shallowly within the pelvis, and the body portion 80 of the implant 78 is positioned between the vagina 222 and the rectum 226. At that point, the excess portions of the arms can then be trimmed, the vaginal incision can be closed, and the external incisions 210 can be closed.

Figure 13:
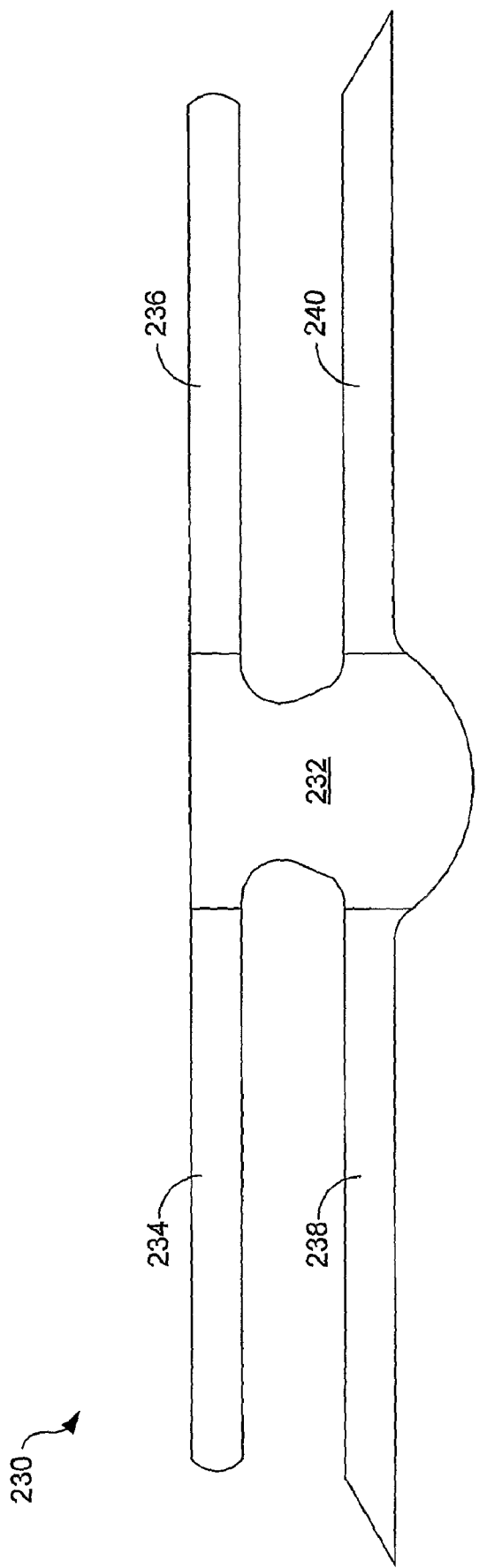
FIG. 13 is a top view of a second embodiment of an anterior implant.
Figure 14:
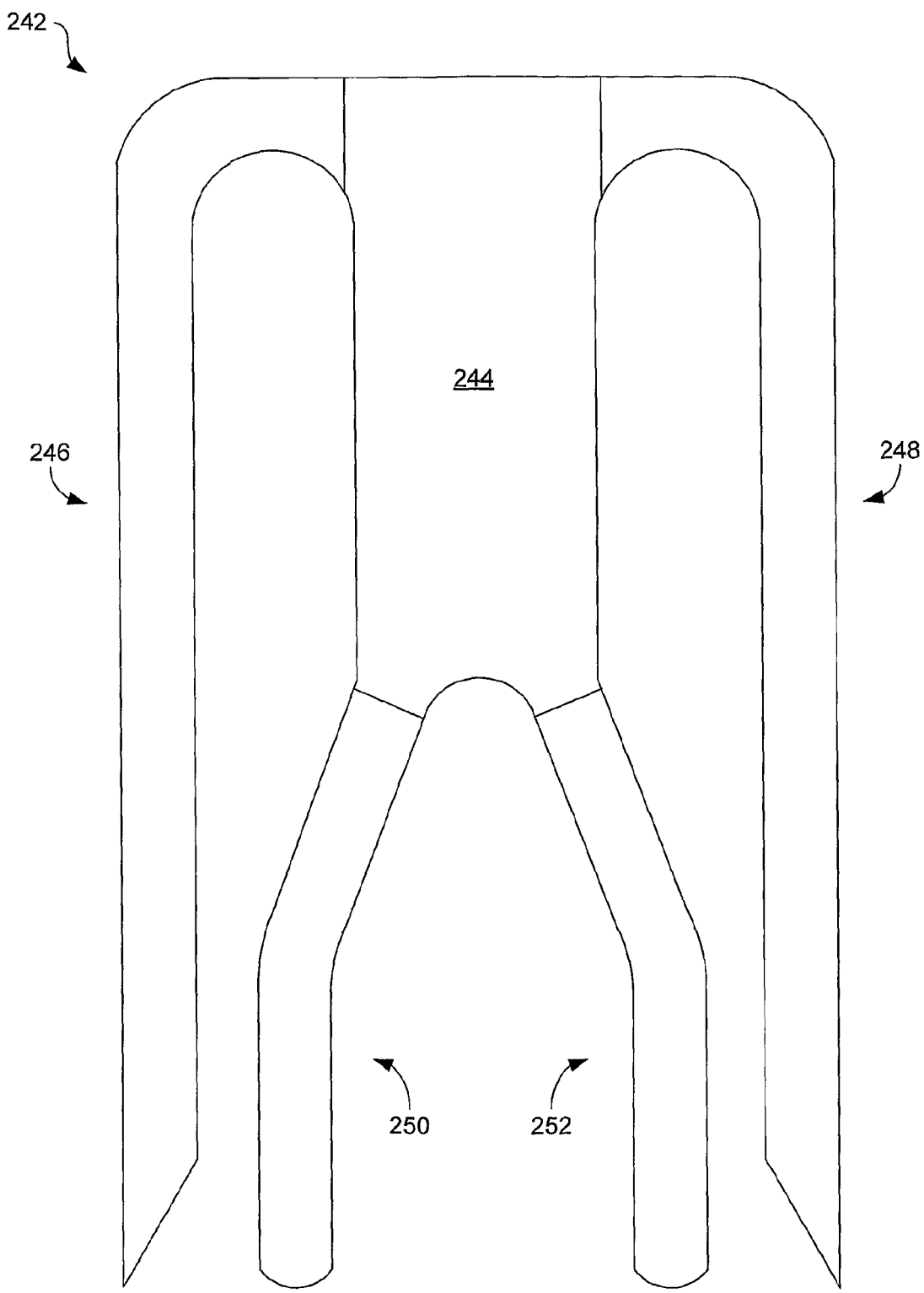
FIG. 14 is a top view of a second embodiment of a posterior implant.

FIGS. 13 and 14 illustrate alternative pelvic implants that comprise both natural and synthetic material. Beginning with FIG. 13, an anterior implant 230 having a shape and dimensions similar to the implant 10 of FIG. 1 is illustrated. Like the implant 10, the implant 230 comprises a body portion 232 from which multiple arms 234, 236, 238, and 240 extend. However, with the implant 230, the body portion 232 is composed substantially exclusively of a natural material while each of the arms 234, 236, 238, and 240 at least comprises a synthetic material. By way of example, the natural material comprises a cross-linked porcine dermal collagen material, such as Pelvicol® surgical implant from Tissue Science Laboratories plc, or Pelvisoft® acellular collogen biomesh produced by Sofradim. In a further alternative, the body portion 232 comprises a layer of natural material that is affixed to a layer of synthetic material. In such a case, the natural material may be positioned so as to face the organ to be supported. In yet another alternative, the body portion 232 comprises two layers of natural material, one provided on either side of a layer of synthetic material. In cases in which natural material is connected to the synthetic material, various connection means may be used such as suturing, stapling, riveting, adhesive, bonding, heat laminating, and the like.

Turning to FIG. 14, a posterior implant 242 having a shape and dimensions similar to the implant 78 of FIG. 3 is illustrated. Like the implant 78, the implant 242 comprises a body portion 244 from which multiple arms 246, 248, 250, and 252 extend. However, with the implant 242, the body portion 244 is composed substantially exclusively of a natural material while each of the arms 246, 248, 250, and 252 at least comprises a synthetic material. By way of example, the natural material comprises a cross-linked porcine dermal collagen material, such as Pelvicol® surgical implant or Pelvisoft® acellular collagen biomesh. In a further alternative, the body portion 244 comprises a layer of natural material that is affixed to a layer of synthetic material. In such a case, the natural material may be positioned so as to face the organ to be supported. In yet another alternative, the body portion 244 comprises two layers of natural material, one provided on either side of a layer of synthetic material. In cases in which natural material is connected to the synthetic material, various connection means may be used such as suturing, stapling, riveting, adhesive, bonding, heat laminating, and the like.

Figure 15:
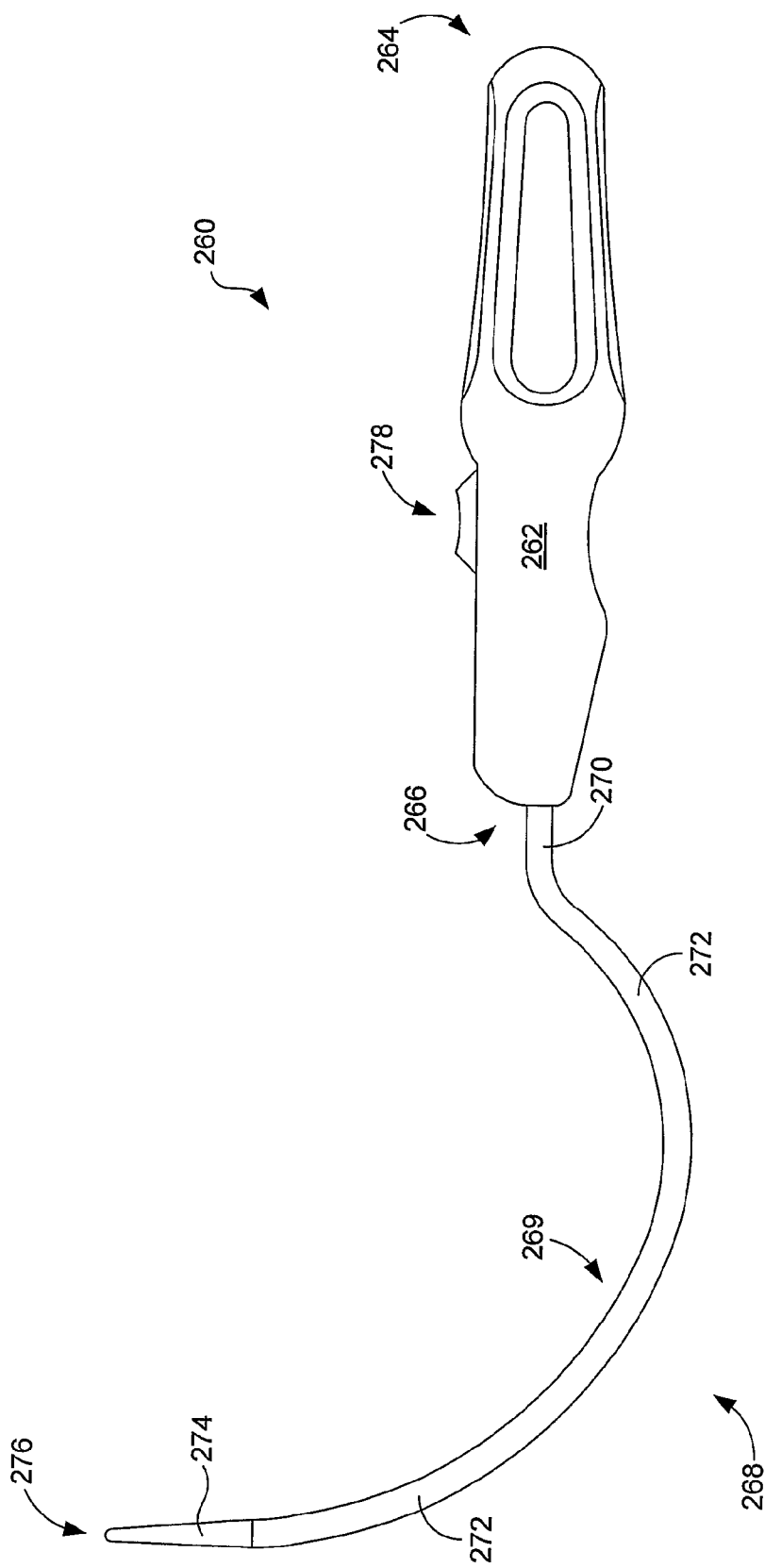
FIG. 15 is a side view of a second embodiment of a posterior introducer.

FIG. 15 illustrates an alternative embodiment of an introducer 260. By way of example, shown is a posterior introducer that can be used to implant a posterior implant, such as implant 78 (FIG. 3). As indicated in FIG. 15, the introducer 260 is similar in construction to the introducer 170 of FIG. 9. Therefore, the introducer 260 comprises a handle 262 that includes a proximal end 264 and a distal end 266. The handle 262 is generally sized and shaped to fit within a surgeon's hand and can be contoured to facilitate firm gripping.

A needle 268 extends from the distal end 266 of the handle 262. The needle 268 comprises a needle body 269 that includes a substantially straight section 270 that directly extends from the handle 262 substantially parallel to a longitudinal axis of the handle (not identified). Extending from the straight section 270 is a curved section that comprises first curved portion 272 adjacent the straight portion 270 that has a relatively small radius of curvature, and a second curved portion 272 distant from the straight portion that has a relatively large radius of curvature.

Positioned at a distal end of the needle body 269 is an extendible tip member 276 that terminates in a blunt tip 278. The tip member 276 is configured for releasable attachment to the needle body 269 and for detachment therefrom such that the tip member can be extended away from the needle body to facilitate association of the needle 268 with an implant. Enabling extension of the tip member 276 is an actuator 278 that is provided on the handle 262. In the embodiment of FIG. 15, the actuator comprises a slide member that can, for example, be operated by the surgeon's thumb.

FIG. 16 illustrates extension of the tip member 276 from the needle body 269. As indicated in FIG. 16, the tip member 276 has been extended away from the needle body 269 in a direction indicated by arrow 280 through manipulation of the actuator 278 in the direction of arrow 282. More particularly, displacement of the actuator 278 has caused similar displacement of a connector member 284 that extends through the needle body 269 (which is hollow) to connect the actuator to the tip member 274. The connector member 284 is flexible so as to conform to the contours of the needle body 269 yet has sufficient column strength to dislodge the tip member 274 from the needle body and extend the tip member from the needle body. By way of example, the connector member 284 comprises a single or multiple metal and/or polymeric wires. In cases in which the connector member is metal, suitable metal materials include nitinol and stainless steel.

FIGS. 17A and 17B illustrate two alternative embodiments for the tip member 274. Both tip members 274' (FIG. 17A) and 274" (FIG. 17B) comprise a tang 286 that seats within the needle body 269 when the tip member is fully retracted. The tang 286 aids in securing the tip member 274', 274" to the needle body 269 as the needle 268 is passed through the soft tissue of the pelvis. Tip member 274' comprises an opening 288 that is provided through an exterior portion of the tip member adjacent the tip 276. In contrast, tip member 274" comprises an opening 290 that is provided through the tang 286.

The introducer 260 can be used to access the vagina in similar manner to that described above in relation to the other introducers. Once the tip member 274 has penetrated the vagina, however, the tip member can be dislodged from the needle body 269 and extended down along the vagina to exteriorize the opening (e.g., opening 288 or 290) to enable attachment of an implant to the tip member. The tip member 274 can then be retracted through the vagina and reconnected to the needle body 269. In embodiments in which an opening is provided through the tip member tang 286, the implant can be at least partially drawn into the needle body 269 to secure the implant.

Figure 18:
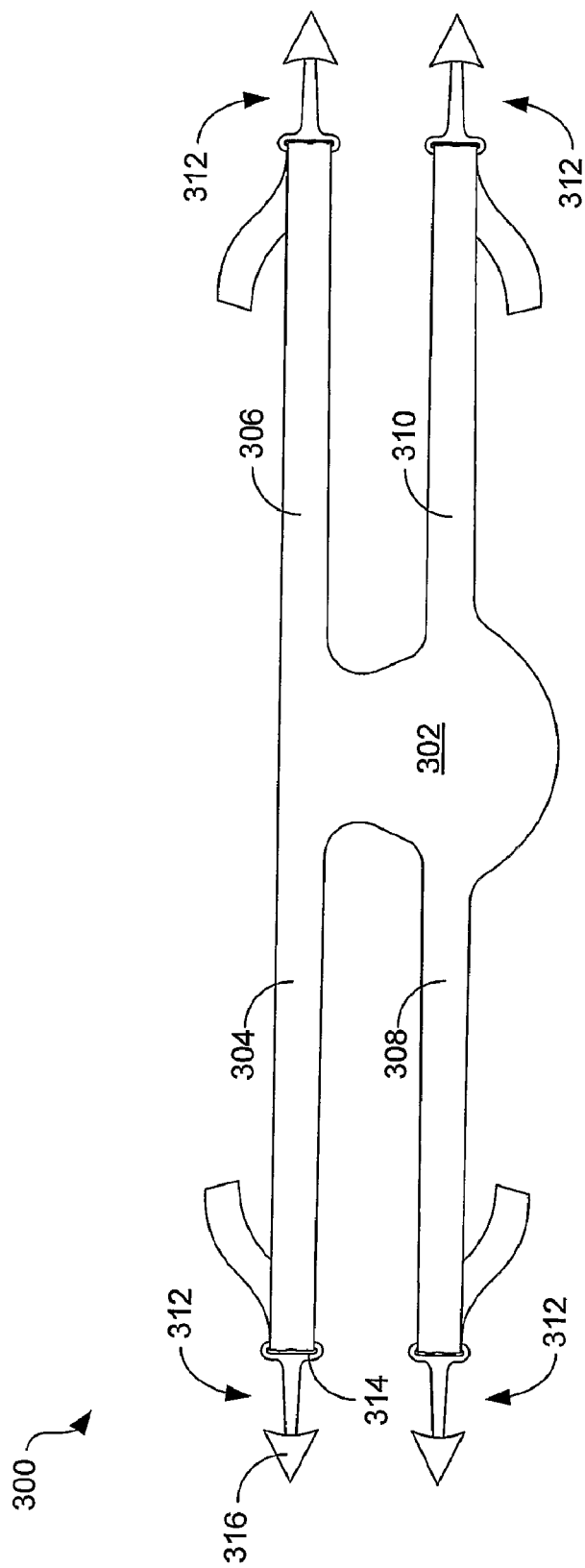
FIG. 18 is a top view of a pelvic implant that comprises soft tissue anchors.

FIG. 18 illustrates a further alternative pelvic implant. More particularly, illustrated is an anterior implant 300 having a shape and dimensions similar to the implant 10 of FIG. 1. Like the implant 10, the implant 300 comprises a body portion 302 from which multiple arms 304, 306, 308, and 310 extend. Attached to each of those arms is an anchor 312 that can be used to secure the ends of the arms within a desired area of soft tissue within the pelvis. In the embodiment of FIG. 18, each anchor 312 comprises an opening 314 through which an arm of an implant can be passed and a sharp tip 316 that can penetrate and be securely lodged within soft tissue. In some embodiments, the opening 314 is sized and configured to limit free passage of the implant arm through the opening. With such a configuration, the surgeon can adjust the length of the arm without having the length later change due to the anchor slipping along the arm.

As described above, procedures other than prolapse repair can be performed using the apparatus described above or similar apparatus. For example, the introducers disclosed herein can be used in some embodiments to introduce an implant intended to treat urinary incontinence. In such a procedure, similar steps can be performed except that the implant can comprise a urethral sling that is positioned below the urethra to provide support to the urethra. In some cases, the anterior implant may also serve to alleviate urinary incontinence.

The invention claimed is:

1. A pelvic implant comprising:
    a body portion configured to support an organ, the body portion defining a plane in a flat configuration and a central axis from a front edge to a rear edge of the body portion about which the implant is substantially symmetric, the rear edge of the body portion including a rearwardly extending rear projection contained in the plane; and
    multiple arms that extend from the body portion, at least one arm being substantially perpendicular to the central axis.

2. The implant of claim 1, wherein the body portion comprises a substantially straight front edge, a rounded rear edge, and opposed lateral edges.

3. The implant of claim 2, wherein the body portion is formed from a mesh material and is coated with a collagen material.

4. The implant of claim 2, wherein the lateral edges are angled relative to the central axis such that the body portion widens from front to back.

5. The implant of claim 1, wherein each of the arms is substantially perpendicular to the central axis.

6. The implant of claim 1, wherein the arms comprise two front arms and two rear arms.

7. The implant of claim 6, wherein the front arms comprise front edges that are contiguous with a front edge of the body portion.

8. The implant of claim 6, wherein the front arms have rounded ends and the rear arms have pointed ends.

9. The implant of claim 6, wherein the front arms are approximately as long as the rear arms.

10. The implant of claim 7, wherein the rear projection extends along the central axis rearwardly of a line contiguous with a rear edge of the two rear arms.

11. The implant of claim 10, wherein the body portion comprises an area of relatively soft mesh material and the arms comprise areas of relatively coarse mesh material.

12. The implant of claim 10, wherein at least the body portion is coated with a film of collagen.

13. An anterior prolapse implant comprising:
- a body portion configured to support a bladder, the body portion defining a central axis about which the implant is substantially symmetric;
- two front arms that extend from the body portion in substantially opposite directions, each of the front arms being substantially perpendicular to the central axis;
- two rear arms that extend from the body portion in substantially opposite directions, each of the rear arms being substantially perpendicular to the central axis and parallel to the front arms; and
- a rear projection contiguous with the body portion that extends rearwardly from the rear arms;
- wherein the implant is formed from synthetic mesh material, the body portion comprising a relatively soft mesh material and the arms comprising relatively coarse mesh material.

14. A posterior prolapse implant comprising:
- an elongated body portion configured to support a rectum, the body portion defining a plane in a flat configuration and a longitudinal axis about which the implant is substantially symmetric;
- two front arms contained in the plane that generally extend from the body portion in a first direction, each front arm including a first section that extends from the body portion at a divergent angle and a second section that extends from the first section in a direction substantially parallel to the longitudinal axis; and
- two rear arms contained in the plane that generally extend from the body portion in the first direction, each of the rear arms including a lateral portion that extends from the body portion in a direction substantially perpendicular to the longitudinal axis and a longitudinal section that extends from the lateral section in a direction substantially parallel to the longitudinal axis;
- wherein the implant is formed from synthetic mesh material, the body portion comprising a relatively soft mesh material and the arms comprising relatively coarse mesh material.

15. The implant of claim 14, wherein the rear arms are approximately twice as long as the front arms.

16. The implant of claim 14, wherein at least the body portion is coated with a film of collagen.

\* \* \* \* \*